United States Patent
Diwu et al.

(10) Patent No.: US 8,318,953 B2
(45) Date of Patent: Nov. 27, 2012

(54) REACTIVE COUMARIN DERIVATIVES AND THEIR USE IN CELLULAR ANALYSES

(75) Inventors: Zhenjun Diwu, Sunnyvale, CA (US); Chunmei Wei, Sunnyvale, CA (US); Qinglin Meng, Sunnyvale, CA (US); Haitao Guo, Santa Clara, CA (US); Jingfang Liao, Foster City, CA (US)

(73) Assignee: AAT Bioquest, Inc., Sunnyvale, CA (US)

( * ) Notice: Subject to any disclaimer, the term of this patent is extended or adjusted under 35 U.S.C. 154(b) by 282 days.

(21) Appl. No.: 12/822,091

(22) Filed: Jun. 23, 2010

(65) Prior Publication Data

US 2011/0318772 A1    Dec. 29, 2011

(51) Int. Cl.
*C07D 405/12* (2006.01)

(52) U.S. Cl. ........................................ 548/525; 549/399
(58) Field of Classification Search .................... 549/399
See application file for complete search history.

(56) References Cited

U.S. PATENT DOCUMENTS

| | | | |
|---|---|---|---|
| 4,956,480 A | | 9/1990 | Robinson |
| 5,741,657 A | * | 4/1998 | Tsien et al. ...................... 435/18 |
| 5,830,912 A | | 11/1998 | Gee et al. |
| 6,034,121 A | * | 3/2000 | O'Mahony et al. ........... 514/456 |
| 6,207,404 B1 | | 3/2001 | Miller et al. |
| 6,566,508 B2 | | 5/2003 | Bentsen et al. |
| 2010/0029017 A1 | * | 2/2010 | Diwu et al. ................... 436/536 |

OTHER PUBLICATIONS

Chemical Abstracts Registry No. 1029773-10-1, indexed in the Registry file on STN CAS Online Jun. 22, 2008.*

* cited by examiner

*Primary Examiner* — Laura L Stockton
(74) *Attorney, Agent, or Firm* — Jeffrey A. McKinney; McKinney Law Group APC

(57) ABSTRACT

Chemically reactive 7-hydroxycoumarin derivatives and their application for analyzing cell function, for example in combination with additional fluorescent labels. The coumarin derivatives exhibit a strong absorption at 405 nm and high fluorescence quantum yields.

4 Claims, 4 Drawing Sheets

Fig. 5
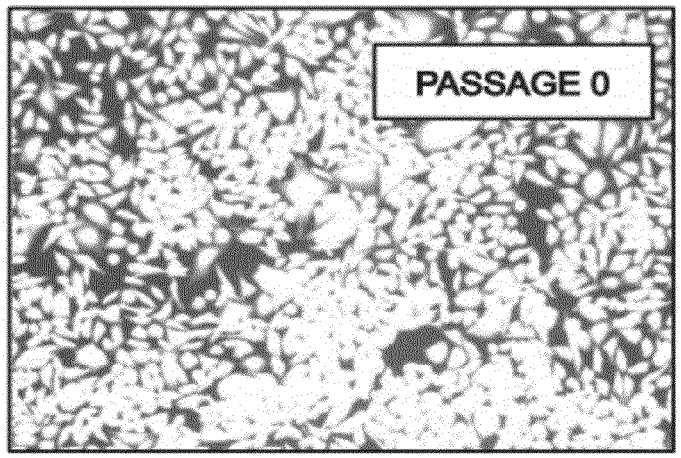
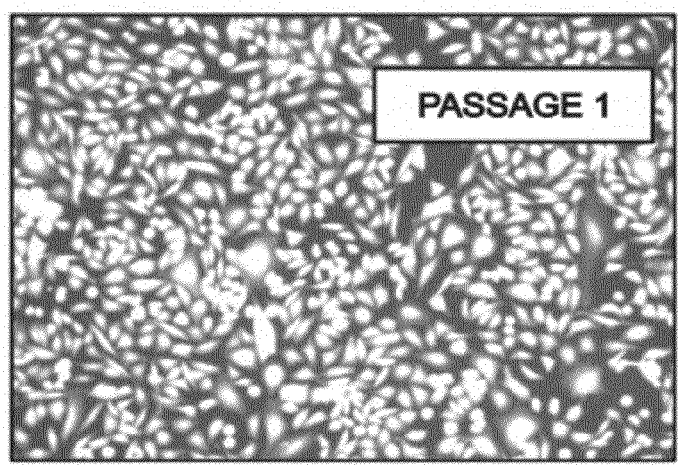
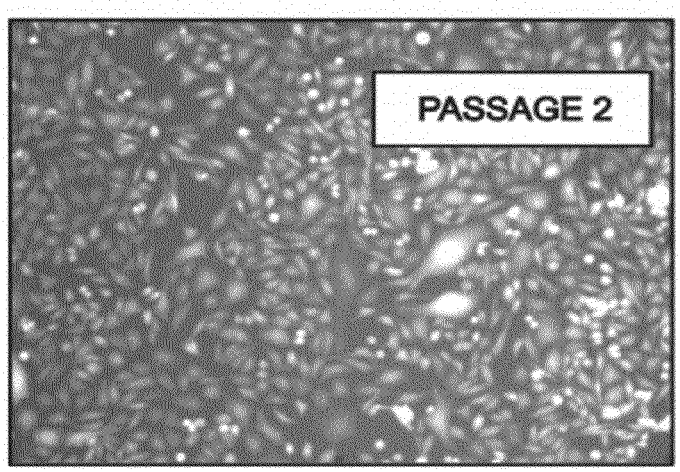

REACTIVE COUMARIN DERIVATIVES AND THEIR USE IN CELLULAR ANALYSES

BACKGROUND

Fluorescent probes are valuable reagents for the analysis and separation of molecules and cells and for the detection and quantification of other materials. A very small number of fluorescent molecules can be detected under optimal circumstances. Barak and Webb visualized fewer than 50 fluorescent lipid analogs associated with the LDL reception of cells using a SIT camera, J. CELL BIOL. 90:595-604 (1981). Flow cytometry can be used to detect fewer than 10,000 fluorescein molecules associated with particles or certain cells (Muirhead, Horan and Poste, BIO/TECHNOLOGY 3:337-356 (1985)). Some specific examples of the application of fluorescent probes are (1) identification and separation of subpopulations of cells in a mixture of cells by the techniques of fluorescence flow cytometry, fluorescence-activated cell sorting and fluorescence microscopy; (2) determination of the concentration of a substance that binds to a second species (e.g., antigen-antibody reactions) in the technique of fluorescence immunoassay; and (3) localization of substances in gels and other insoluble supports by the techniques of fluorescence staining. These techniques are described by Herzenberg et al., "CELLULAR IMMUNOLOGY" 3rd ed., Chapter 22; Blackwell Scientific Publications (1978); and by Goldman, "FLUORESCENCE ANTIBODY METHODS" Academic Press, New York, (1968); and by Taylor et al., APPLICATIONS OF FLUORESCENCE IN THE BIOMEDICAL SCIENCES, Alan Liss Inc. (1986).

When employing fluorescent enzyme substrates for the above purposes, there are many constraints on the choice of a fluorescent enzyme substrate. One constraint is the absorption and emission characteristics of the fluorophore generated from a fluorescent enzyme substrate, since many ligands, receptors, and materials in the sample under test, e.g. blood, urine, cerebrospinal fluid, will fluoresce and interfere with an accurate determination of the fluorescence of the fluorescent label. This phenomenon is called autofluorescence or background fluorescence. Another consideration is the ability to keep the fluorescent enzyme substrates and their enzymatic products inside of cells through the conjugation of cellular components with the reactive fluorescent substrates and/or their enzymatic products. A third consideration is the quantum efficiency of the products generated from the enzyme substrates which should be high for sensitive detection. A fourth consideration is the light absorbing capability, or extinction coefficient, of the fluorescent products derived from the reaction of the enzyme substrates, which should also be as large as possible.

The applicability and value of the methods indicated above are closely tied to the availability of suitable fluorescent enzyme substrates. In particular, there is a need for fluorescent substances that can be excited by commercial viable laser sources such as the violet laser (405 nm), argon laser (488 nm) and He—Ne laser (633 nm). There are many fluorescent enzyme substrates developed for the argon laser (488 nm excitation) and He—Ne laser (633 nm excitation). For example, fluorescein-based enzyme substrates, which are well excited by 488 nm argon laser, are useful emitters in the green region. CFSE, a reactive fluorescein-based esterase substrate, is widely used for monitoring cell proliferations with argon laser excitation, e.g., Asquith et al., Proc. Biol. Sci., 2006, 273, 1165; Cao et al., Cytometry A, 2009, 75, 975; Lyons, J. Immunol. Methods, 2000, 243, 147; Witkowski, in "Current Protocols in Cytometry" Chapter 9, Unit 925. However, there are few reactive fluorescent enzyme substrates available for the 405 nm violet laser. Brightly fluorescent enzyme substrates permit detection or location of the attached materials with great sensitivity. Certain coumarin enzyme substrates have demonstrated utilities for a variety of biological detection applications, e.g., U.S. Pat. No. 6,566,508 to Bentsen et al. (2003); U.S. Pat. No. 6,207,404 to Miller et al. (2001); U.S. Pat. No. 5,830,912 to Gee et al. and U.S. Pat. No. 4,956,480 to Robinson (1990).

SUMMARY

We have discovered chemically reactive 7-hydroxycoumarin derivatives that can be used to generate fluorophores in live cells. In particular, reactive enzyme substrates derived from these 7-hydroxycoumarins can be used to monitor a variety of cellular functions (e.g., cell proliferation, cell cytotoxicity and cell viability tests). These violet laser-excitable 7-hydroxycoumarin derivatives can be used with existing fluorescent probes that are excited by the argon laser (488 nm) and He—Ne laser (633 nm) to enable the multicolor analysis of combinations of multiple distinct cellular functions.

DEFINITIONS

The following definitions are set forth to illustrate and define the meaning and scope of the various terms used to describe the invention herein.

The term "alkyl" as used herein, by itself or as part of another group, refers to straight, branched chain or cyclic radicals having up to 50 carbons, unless the chain length or ring size is limited thereto, such as methyl, ethyl, propyl, cyclopropyl, isopropyl, butyl, t-butyl, isobutyl, pentyl, hexyl, cyclohexyl, isohexyl, heptyl, 4,4-dimethylpentyl, octyl, 2,2, 4-trimethylpentyl, nonyl, and decyl, among others. The term "alkyl" broadly includes "alkylene," "alkenyl," "alkenylene," "alkynyl" and "alkynylene."

The term "alkylene" as employed herein, by itself or as part of another group, refers to straight, branched chain or cyclic divalent radicals having up to 50 carbons, unless the chain length or ring size is limited thereto. Typical examples include methylene (—$CH_2$—), ethylene (—$CH_2CH_2$—), hexylene, heptylene, octylene, nonylene, and decylene, among others.

The term "alkenyl" as used herein, by itself or as part of another group, means a straight, branched chain or cyclic radical having 2-50 carbon atoms and one or more carbon-carbon double bonds, unless the chain length or ring size is limited thereto, such as ethenyl, 1-propenyl, 2-propenyl, 2-methyl-1-propenyl, 1-butenyl, and 2-butenyl, among others. The alkenyl chain may be 2 to 10 carbon atoms in length. Alternatively, the alkenyl chain may be 2 to 4 carbon atoms in length.

The term "alkenylene" as used herein, by itself or as part of another group, means straight, branched chain or cyclic divalent radical having 2-50 carbon atoms, unless the chain length or ring size is limited thereto, said straight, branched chain or cyclic radical containing at least one carbon-carbon double bond. Typical examples include ethenylene (—CH=CH—), propenylene (—CH=$CHCH_2$— and —$CH_2$CH=CH—), n-butenylene, and 3-methyl-2-pentenylene, hexenylene, heptenylene, octenylene, nonenylene, and decenylene, among others.

The term "alkynyl" as used herein, by itself or as part of another group, means a straight, branched chain or cyclic radical of 2-50 carbon atoms, unless the chain length or ring size is limited thereto, having at least one carbon-carbon triple bond between two of the carbon atoms in the chain, such as acetylenyl, 1-propynyl, and 2-propynyl, among others. The alkynyl chain may be 2 to 10 carbon atoms in length. Alternatively, the alkynyl chain may be from 2 to 4 carbon atoms in length.

The term "alkynylene" as used herein, by itself or as part of another group, means a straight, branched chain or cyclic divalent radical having 2-50 carbon atoms, unless the chain length or ring size is limited thereto, that contains at least one carbon-carbon triple bond. Typical examples include ethynylene (—C≡C—), propynylene (—C≡CCH$_2$— and —CH$_2$C≡C—), n-butynylene, 4-methyl-2-pentynylene, 1-butynylene, 2-butynylene, 3-butynylene, 4-butynylene, pentynylene, hexynylene, heptynylene, octynylene, nonynylene, and decynylene, among others.

The term "alkoxy" as used herein, by itself or as part of another group, refers to any of the above radicals linked via an oxygen atom. Typical examples include methoxy, ethoxy, isopropyloxy, sec-butyloxy, n-butyloxy, t-butyloxy, n-pentyloxy, 2-methylbutyloxy, 3-methylbutyloxy, n-hexyloxy, and 2-ethylbutyloxy, among others. Alkoxy also may include PEG groups (—OCH$_2$CH$_2$O—) or alkyl moieties that contain more than one oxygen atom.

The term "aryl" as employed herein, by itself or as part of another group, refers to an aryl or aromatic ring system containing 1 to 4 unsaturated rings (each ring containing 6 conjugated carbon atoms and no heteroatoms) that are optionally fused to each other or bonded to each other by carbon-carbon single bonds, that is optionally further substituted as described below. Examples of aryl ring systems include, but are not limited to, substituted or unsubstituted derivatives of phenyl, biphenyl, o-, m-, or p-terphenyl, 1-naphthyl, 2-naphthyl, 1-, 2-, or 9-anthryl, 1-, 2-, 3-, 4-, or 9-phenanthrenyl and 1-, 2- or 4-pyrenyl. Aryl substituents may include phenyl, substituted phenyl, naphthyl or substituted naphthyl.

The term "heteroatom" as used herein, by itself or as part of another group, means an oxygen atom ("O"), a sulfur atom ("S") or a nitrogen atom ("N"). It will be recognized that when the heteroatom is nitrogen, it may form an NR$^1$R$^2$ moiety, where R$^1$ and R$^2$ are, independently from one another, hydrogen or alkyl, or together with the nitrogen to which they are bound, form a saturated or unsaturated 5-, 6-, or 7-membered ring.

The term "heterocycle" or the interchangeable "heteroaryl" as employed herein, by itself or as part of another group, refers to groups having 5 to 14 ring atoms; 6, 10 or 14 π electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, carbazolyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups).

Any aryl or heteroaryl ring system is unsubstituted or optionally and independently substituted by any synthetically accessible and chemically stable combination of substituents, such as H, halogen, cyano, sulfo, alkali or ammonium salt of sulfo, nitro, carboxy, alkyl, perfluoroalkyl, alkoxy, alkylthio, amino, monoalkylamino, dialkylamino or alkylamido, the alkyl portions of which having 18 or fewer carbons.

The terms "halogen" or "halo" as employed herein, by itself or as part of another group, refers to chlorine, bromine, fluorine or iodine.

The terms "amino" or "amine" include NH$_2$, "monoalkylamine" or "monoalkylamino," and "dialkylamine" or "dialkylamino". The terms "monoalkylamine" and "monoalkylamino," "dialkylamine" and "dialkylamino" as employed herein, by itself or as part of another group, refers to the group NH$_2$ where one hydrogen has been replaced by an alkyl group, as defined above.

The term "hydroxyalkyl," as employed herein, by itself or as part of another group, refers to an alkyl group where one or more hydrogens thereof are substituted by one or more hydroxyl moieties.

The term "haloalkyl," as employed herein, by itself or as part of another group, refers to an alkyl group where one or more hydrogens thereof are substituted by one or more halo moieties. Typical examples include chloromethyl, fluoromethyl, difluoromethyl, trifluoromethyl, trichloroethyl, trifluoroethyl, fluoropropyl, and bromobutyl, among others.

The term "haloalkenyl," as employed herein, by itself or as part of another group, refers to an alkenyl group where one or more hydrogens thereof are substituted by one or more halo moieties.

The term "haloalkynyl," as employed herein, by itself or as part of another group, refers to an alkynyl group where one or more hydrogens thereof are substituted by one or more halo moieties.

The term "carboxyalkyl," as employed herein, by itself or as part of another group, refers to an alkyl group where one or more hydrogens thereof are substituted by one or more carboxylic acid moieties.

The term "fluorophore or fluorophore moiety" as used herein, by itself or as part of another group, means a molecule or a portion of a molecule which exhibits fluorescence. By fluorescence is meant that the molecule or portion of a molecule can absorb excitation energy having a given wavelength and emit energy at a different wavelength. The intensity and wavelength of the emitted energy depend on the fluorophore, the chemical environment of the fluorophore, and the specific excitation energy used. Exemplary fluorophores include, but are not limited to, fluoresceins, rhodamines, coumarins, oxazines, cyanines, pyrenes, and other polycyclic aromatic molecules.

The terms "colored enzyme substrate" and "fluorescent enzyme substrate" as used herein refers to both enzyme substrates that are intrinsically colored or fluorescent, and to enzyme substrates that are chromogenic, and/or fluorogenic. That is, "fluorescent enzyme substrate" may refer to an enzyme substrate that only becomes fluorescent upon action by the appropriate enzyme.

The term "coumarin," or "coumarin derivative," as used herein, by itself or as part of another group, means any compounds or substituents that contain one or more of the following fused ring structure or its derivatives:

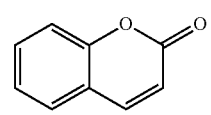

Coumarin

The term "7-hydroxycoumarin" as used herein, by itself or as part of another group, means any compounds or substituents that contain one or more of the following fused ring structure or its derivatives:

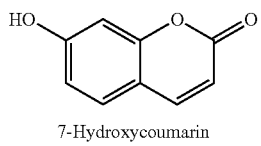

7-Hydroxycoumarin

It is to be understood that the disclosed coumarin compounds have been drawn in one or another particular electronic resonance structure. Every aspect of the compounds described herein applies equally to enzyme substrates that are formally drawn with other permitted resonance structures, as the electronic charge on the subject compounds are delocalized throughout the compound itself.

The term "substituted," as used herein, refers to the formal replacement of a hydrogen on a chemical moiety or functional group with an alternative radical. Where a compound, chemical moiety or functional group is described as substituted, the alternative radical substituent moiety is generally selected from the group consisting of hydroxy, oxo, nitro, trifluoromethyl, halogen, alkoxy, alkylenedioxy, aminoalkyl, aminoalkoxy, amino, monoalkylamino, dialkylamino, alkylcarbonylamino, alkoxycarbonylamino, alkoxycarbonyl, carboxy, hydroxyalkoxy, alkoxyalkoxy, monoalkylaminoalkoxy, dialkylaminoalkoxymono(carboxyalkyl)amino, bis(carboxyalkyl)amino, alkoxycarbonyl, alkynylcarbonyl, alkylsulfonyl, alkenylsulfonyl, alkynylsulfonyl, arylsulfonyl, alkylsulfonyl, alkylsulfinyl, alkylsulfonamido, arylsulfonamido, alkylsulfonamido, carboxyalkoxy, carboxyalkyl, carboxyalkylamino, cyano, trifluoromethoxy, perfluoroethoxy, guanidine, amidino, oxyguanidino, alkylimino, formylimino, acyl nitrile, acyl azide, acetyl azide, dichlorotriazene, isothiocyante, sulfonyl halide, sulfosuccinimidyl ester, isocyante, acyl halide, aldehyde, haloacetamide, maleimido, aziridinyl, alkylthio (disulfide), acrylo, haloalkylcarbonyl, boronate, hydrazide, semicarbazide, carbohydrazide, arylalkyl, heteroarylalkyl, cycloalkylalkyl, cycloalkenylalkyl, cycloheteroalkylalkyl, and cycloheteroalkenylalkyl.

DESCRIPTION OF DRAWINGS

FIG. 5 shows the dye loading of compound ES 9 into cells. Compound ES 9 is dissolved in anhydrous DMSO to make 5 mM stock solution, and diluted in PBS buffer to make 5 µM dye loading solution. CPA cells are loaded with the dye loading solution of Compound ES9 at 37° C. for 1 hour. The cells are washed with PBS buffer to remove serum. Some wells of the cells are trypsinized for passage. Imaging is taken after 1 hour (passage 0), passage 1 and passage 2 after the dye loading using the filter set of excitation (410 nm, band pass) and emission (>450 nm, long pass).

DESCRIPTION OF PREFERRED EMBODIMENTS

Figure 1:
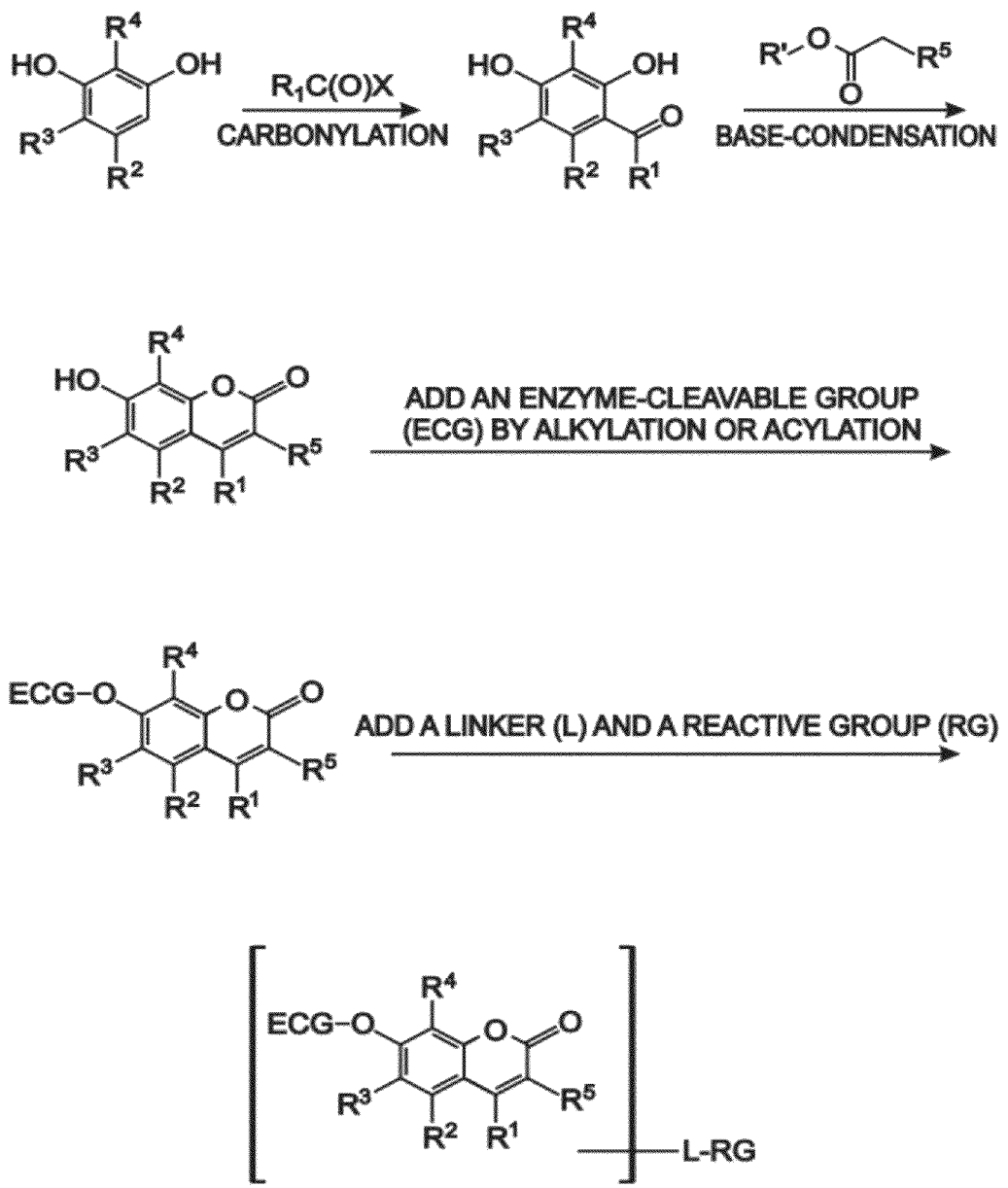
FIG. 1 is a reaction scheme for the synthesis of reactive 7-hydroxycoumarin enzyme substrates by the base-catalyzed condensation of 4-carbonylresorcinols with a heterocycle acetatic acid or a carbonylacetate derivative. These basic structures are optionally further substituted, during or after synthesis, to give the desired coumarin enzyme substrate with proper substituents.

Although some 7-hydroxy coumarins were used for enzyme activity detection (U.S. Pat. No. 6,566,508), these coumarin substrates were primarily used in solutions, cell extracts or for analyzing the activities of isolated or purified enzymes. When such existing coumarin substrates were used for analyzing cellular functions or cellular activities in live cells, the fluorogenic substrates and the fluorescent products of their enzymatic cleavage tended to leak out of cells rapidly, making them unsuitable for tracking cellular functions for long term in live cells.

We have found that 7-hydroxycoumarin enzyme substrates modified with a chemically reactive functional group are well-retained within living cells without significant leakage. Furthermore, the 7-hydroxycoumarin fluorophores resulting from enzymatic cleavage have strong absorptions at ~405 nm and are highly fluorescent. In addition, the halogenation of the 7-hydroxycoumarins significantly decreases the pKa of the coumarin fluorophore, so that the chemically reactive coumarin substrates of this disclosure generate free fluorophores having their maximum fluorescence in the range of physiological pH.

The 7-hydroxycoumarin substrates are only weakly fluorescent but upon enzymatic cleavage generate a free coumarin fluorophore that is substantially fluorescent in live cells. These fluorophores typically exhibit an absorbance maxima close to 405 nm, such that the spectral properties of the free coumarin fluorophores can be selected to match the principal emission lines of the violet laser, and the enhanced fluorescence intensity of the reactive hydroxycoumarin fluorophores leads directly to greater assay sensitivity.

The present disclosure is directed to chemically reactive 7-hydroxycoumarin enzyme substrates. These coumarin enzyme substrates are used to locate, detect, monitor and track cellular functions. Kits incorporating such enzyme substrates may facilitate their use in such methods.

The enzyme substrates of the disclosure are typically described by Formula 1:

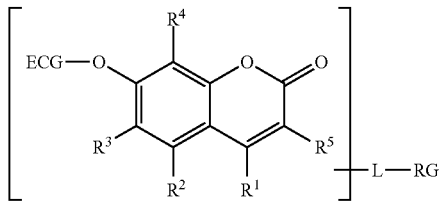

Formula 1 where the ECG moiety is an esterase-cleavable group. An esterase-cleavable group is a functional group that is capable of being cleaved or removed by an esterase enzyme. The generally poorly fluorescent substrate undergoes hydrolytic cleavage of the ECG-O bond, generating a hydroxyl moiety on the resulting highly fluorescent coumarin. Generally, the ECG includes an ester, typically an alkyl ester. The ECG is generally selected to be removable only by the action of an esterase enzyme, and is only removed when an esterase enzyme is present.

L is a covalent linkage between RG and the coumarin, where RG is a chemically reactive group, as described below. At least one of the substituents $R^1$, $R^2$, $R^3$ and $R^4$ is or is modified to be L-RG.

Where substituents $R^1$, $R^2$, $R^3$ and $R^4$ are not a reactive group, they are independently H, halogen, alkoxy, aryloxy, thiol, alkylthiol, arylthiol, azido, amino, hydroxy, sulfonyl, phosphonyl, boronic acid, or alkyl, or alkoxy that is itself optionally substituted one or more times by halogen, amino, hydroxy, sulfonyl, phosphonyl, carbonyl or boronic acid. The $R^5$ substituent is a carbonyl or a heterocycle that is directly conjugated to the coumarin. For example, $R^5$ may be one of the following ring systems, among others:

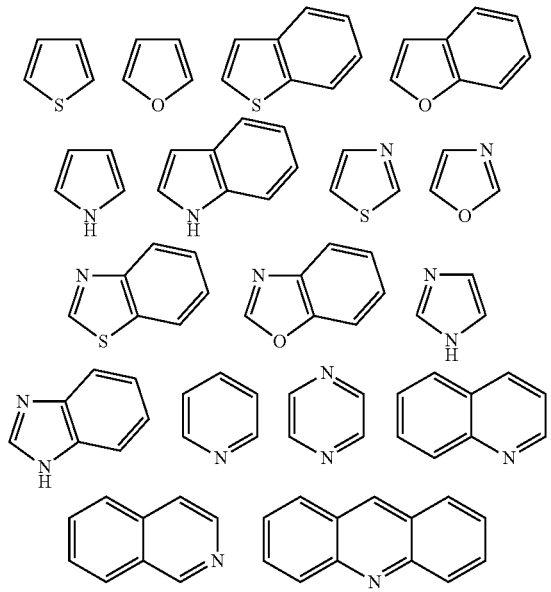

A comprehensive list of suitable heterocycle moieties is readily available in the literature (Alan R. Katritzky, Comprehensive Heterocyclic Chemistry: The Structure, Reactions, Synthesis, and Uses of Heterocyclic Compounds, Pergamon, 1984).

In one aspect of the enzyme substrates, the linker L is a single bond or an aliphatic spacer of less than 20 carbons.

In yet another aspect, the reactive coumarin enzyme substrate is described by Formula 2:

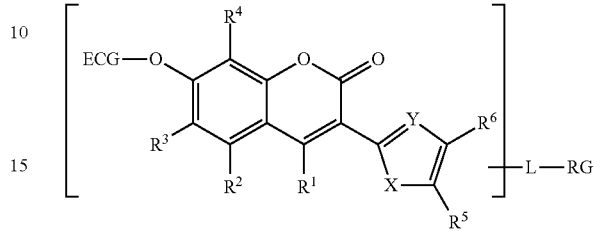

Formula 2 wherein ECG is an esterase-cleavable group, L is a covalent linkage between RG and the coumarin, and RG is a chemically reactive group.

The X moiety is O, S or $NR^{10}$, and the Y moiety is N or $CR^{11}$.

The $R^1$, $R^2$, $R^3$, $R^4$, $R^5$, and $R^6$ are independently H, halogen, alkoxy, aryloxy, thiol, alkylthiol, arylthiol, azido, amino, hydroxy, sulfonyl, phosphonyl or boronic acid, or alkyl, or alkoxy that is itself optionally substituted one or more times by halogen, amino, hydroxy, sulfonyl, phosphonyl, carbonyl or boronic acid. Alternatively or in addition, the $R^5$ substituent may further form an aryl or heteroaryl ring with $R^6$. $R^{10}$ and $R^{11}$ are independently a hydrogen or an alkyl. For all such compounds of Formula 2, at least one of $R^1$, $R^2$, $R^3$, $R^4$, $R^5$, $R^6$, $R^{10}$ and $R^{11}$ is or is substituted by RG.

In yet another aspect, the reactive coumarin enzyme substrate is described by Formula 3:

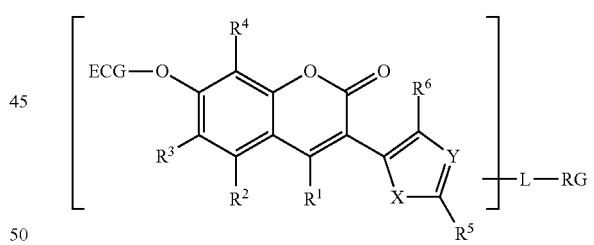

Formula 3 where ECG is an esterase-cleavable group, L is a linker between RG and the coumarin, and RG is a chemically reactive group.

The X moiety is O, S or $NR^{10}$, and the Y moiety is N or $CR^{11}$.

The $R^1$, $R^2$, $R^3$, $R^4$, $R^5$, and $R^6$ substituents are independently H, halogen, alkoxy, aryloxy, thiol, alkylthiol, arylthiol, azido, amino, hydroxy, sulfonyl, phosphonyl or boronic acid, or alkyl, or alkoxy that is itself optionally substituted one or more times by halogen, amino, hydroxy, sulfonyl, phosphonyl, carbonyl or boronic acid. $R^{10}$ and $R^{11}$ are independently a hydrogen or an alkyl. For all such compounds of Formula 3, at least one of $R^1$, $R^2$, $R^3$, $R^4$, $R^5$, $R^6$, $R^{10}$ and $R^{11}$ is or is substituted by RG.

In yet another aspect, the reactive coumarin enzyme substrate is described by Formula 4:

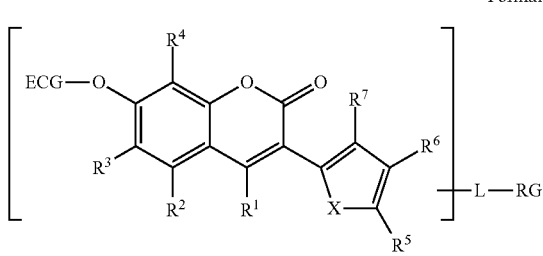

Formula 4 where ECG is an esterase-cleavable group, L is a linker between RG and the coumarin, and RG is a chemically reactive group.

The X moiety is O, S or $NR^{10}$.

The $R^1$, $R^2$, $R^3$, $R^4$, $R^5$, $R^6$, and $R^7$ substituents are independently H, halogen, alkoxy, aryloxy, thiol, alkylthiol, arylthiol, azido, amino, hydroxy, sulfonyl, phosphonyl or boronic acid, or alkyl, or alkoxy that is itself optionally substituted one or more times by halogen, amino, hydroxy, sulfonyl, phosphonyl, carbonyl or boronic acid. Alternatively, or in addition, R5 in combination with $R^6$ form an aryl or heteroaryl ring, or $R^6$ may further form an aryl or heteroaryl ring with $R^7$. $R^{10}$ is a hydrogen or an alkyl.

For all such compounds of Formula 4, at least one of $R^1$, $R^2$, $R^3$, $R^4$, $R^5$, $R^6$, $R^7$, $R^{10}$ and $R^{11}$ is or is substituted by RG.

In yet another aspect, the reactive coumarin enzyme substrate is described by Formula 5:

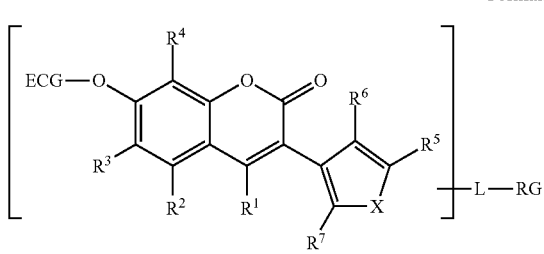

Formula 5 where ECG is an esterase-cleavable group, L is a linker between RG and the coumarin, and RG is a chemically reactive group.

The X moiety is O, S or $NR^{10}$.

The $R^1$, $R^2$, $R^3$, $R^4$, $R^5$, $R^6$, and $R^7$ substituents are independently H, halogen, alkoxy, aryloxy, thiol, alkylthiol, arylthiol, azido, amino, hydroxy, sulfonyl, phosphonyl or boronic acid, or alkyl, or alkoxy that is itself optionally substituted one or more times by halogen, amino, hydroxy, sulfonyl, phosphonyl, carbonyl or boronic acid. Alternatively, or in addition, $R^5$ in combination with $R^6$ form an aryl or heteroaryl ring, or $R^6$ may further form an aryl or heteroaryl ring with $R^7$. $R^{10}$ is a hydrogen or an alkyl.

For all such compounds of Formula 5, at least one of $R^1$, $R^2$, $R^3$, $R^4$, $R^5$, $R^6$, $R^7$, $R^{10}$ and $R^{11}$ is or is substituted by RG.

In yet another aspect, the reactive coumarin enzyme substrate is described by Formula 6:

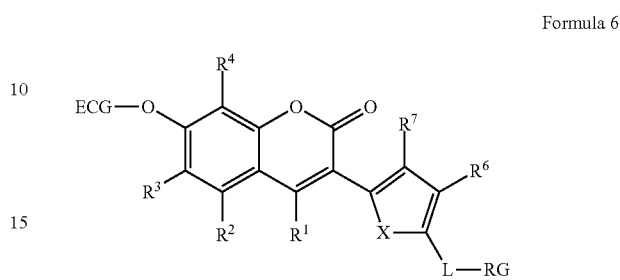

Formula 6 where ECG is an esterase-cleavable group.

The covalent linkage L is a single covalent bond, an alkyl, alkoxy, a thioalkyl, an amino acid, polyamine or a polyethyleneglycol, an arylalky, an aryl, or heteroaryl. RG is a chemically reactive group.

The X moiety is O, S or $NR^{10}$.

The substituents $R^1$, $R^2$, $R^3$, $R^4$, $R^6$, and $R^7$ are independently hydrogen, chloro, fluoro or cyano. Alternatively, $R^6$ in combination with $R^7$ may further form an aryl or heteroaryl ring. $R^{10}$ is an alkyl.

In yet another aspect, the reactive coumarin enzyme substrate is described by Formula 7:

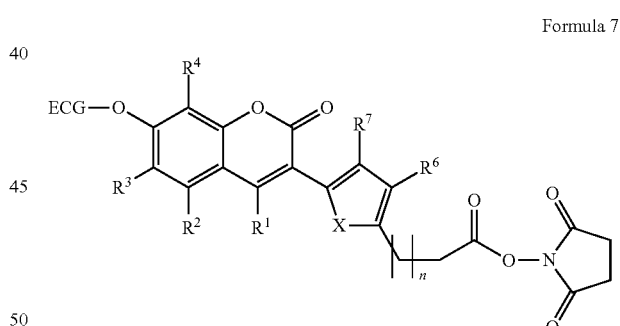

Formula 7 where X is O, S. The esterase-cleavable group ECG is acetyl, acetoxymethyl or a lower acyl. The integer n is 1-10.

The substituents $R^3$, $R^4$, $R^6$ and $R^7$ are independently hydrogen, halogen, alkoxy, aryloxy, thiol, alkylthiol, arylthiol, azido, amino, hydroxy, sulfonyl, phosphonyl or boronic acid, or alkyl, or alkoxy that is itself optionally substituted one or more times by halogen, amino, hydroxy, sulfonyl, phosphonyl, carbonyl or boronic acid. Alternatively, the $R^6$ substituents in combination with $R^7$ may further form an aryl or heteroaryl ring with $R^{11}$.

In yet another aspect, the reactive coumarin enzyme substrate is described by Formula 8:

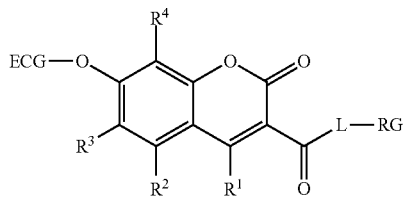

Formula 8 where ECG is an esterase-cleavable group. L is a covalent linkage between RG and the coumarin compound, and RG is a chemically reactive group.

X is O, S or $NR^{10}$.

$R^1$, $R^2$, $R^3$, $R^4$, $R^5$, $R^6$, and $R^7$ are independently H, halogen, alkyl, alkoxy, aryloxy, thiol, alkylthiol, arylthiol, azido, amino, hydroxy, sulfonyl, phosphonyl or boronic acid; $R^5$ may further form an aryl or heteroaryl ring with $R^6$; $R^6$ may further form an aryl or heteroaryl ring with $R^7$, $R^{10}$ is a hydrogen or an alkyl, provided that at least one of $R^1$, $R^2$, $R^3$, $R^4$, $R^5$, $R^6$, $R^7$, and $R^{10}$ is or is substituted by RG.

In yet another aspect, the reactive coumarin enzyme substrate is described by Formula 9:

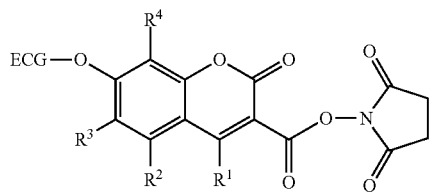

Formula 9 where ECG is acetyl, acetoxymethyl, a lower acyl, glycosidyl, or a lower alkyl. The substituents $R^1$, $R^2$, $R^3$ and $R^4$ are independently hydrogen, chloro, fluoro or cyano, provided that at least one of $R^1$, $R^2$, $R^3$ and $R^4$ is non-hydrogen.

As discussed above, the coumarin enzyme substrates of the present disclosure may be substituted by one or more chemically reactive groups (RG). Typically, the coumarin enzyme substrate of the disclosure is substituted by only one RG.

Typically, the enzyme substrates disclosed herein are substituted by at least one L-RG, where RG is the reactive group that is attached to the enzyme substrate by a covalent linkage L. In certain embodiments, the covalent linkage attaching the enzyme substrate to RG contains multiple intervening atoms that serve as a Linker L. The enzyme substrates with a RG label a wide variety of organic or inorganic substances that contain or are modified to contain functional groups with suitable reactivity, resulting in chemical attachment of the conjugated substance. As used herein, "reactive group (RG)" means a moiety on the compound that is capable of chemically reacting with a functional group on a different compound to form a covalent linkage. Typically the reactive group is an electrophile or nucleophile that can form a covalent linkage through exposure to the corresponding functional group that is a nucleophile or electrophile, respectively. Alternatively, the reactive group is a photoactivatable group, and becomes chemically reactive only after illumination with light of an appropriate wavelength. Typically, the conjugation reaction between the reactive enzyme substrate and the substance to be conjugated results in one or more atoms of the reactive group RG to be incorporated into a new linkage L attaching the enzyme substrate to the conjugated substance. Selected examples of reactive groups and linkages are shown in Table 1, where the reaction of an electrophilic group and a nucleophilic group yields a covalent linkage.

TABLE 1

Examples of RG groups to useful covalent linkages

| Electrophilic Group | Nucleophilic Group | Resulting Conjugate |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COW, where W is a good leaving group (e.g., succinimidyloxy (—$OC_4H_4O_2$) sulfosuccinimidyloxy (—$OC_4H_3O_2$—$SO_3H$), -1-oxybenzotriazolyl (—$OC_6H_4N_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOAlk or —OCN($Alk_1$)NH($Alk_2$), where $Alk_1$ and $Alk_2$, which may be the same or different, are $C_1$-$C_{20}$ alkyl, $C_1$-$C_{20}$ perfluoroalkyl, or $C_1$-$C_{20}$ alkoxy; or cyclohexyl, 3-dimethylaminopropyl, or N-morpholinoethyl).
**Acyl azides can also rearrange to isocyanates.

The selection of a particular reactive group for the enzyme substrate typically depends on the cell types to be tested. Typically, an appropriate RG will react with an amine, a thiol, an alcohol, an aldehyde or a ketone. Preferably RG reacts with an amine or a thiol functional group. In one embodiment, RG is an acrylamide, an activated ester of a carboxylic acid (typically a succinimidyl ester of a carboxylic acid), an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, an imido ester, an isocyanate, an isothiocyanate, or a maleimide.

Where the reactive group is a photoactivatable group, such as an azide, diazirinyl, azidoaryl, or psoralen derivative, the enzyme substrate becomes chemically reactive only after illumination with light of an appropriate wavelength. Where RG is an activated ester of a carboxylic acid, a maleimide or a haloacetamide, the reactive enzyme substrate is particularly useful for mammalian cells. Preferably, RG is a succinimidyl ester of a carboxylic acid.

Synthesis

Figure 2:
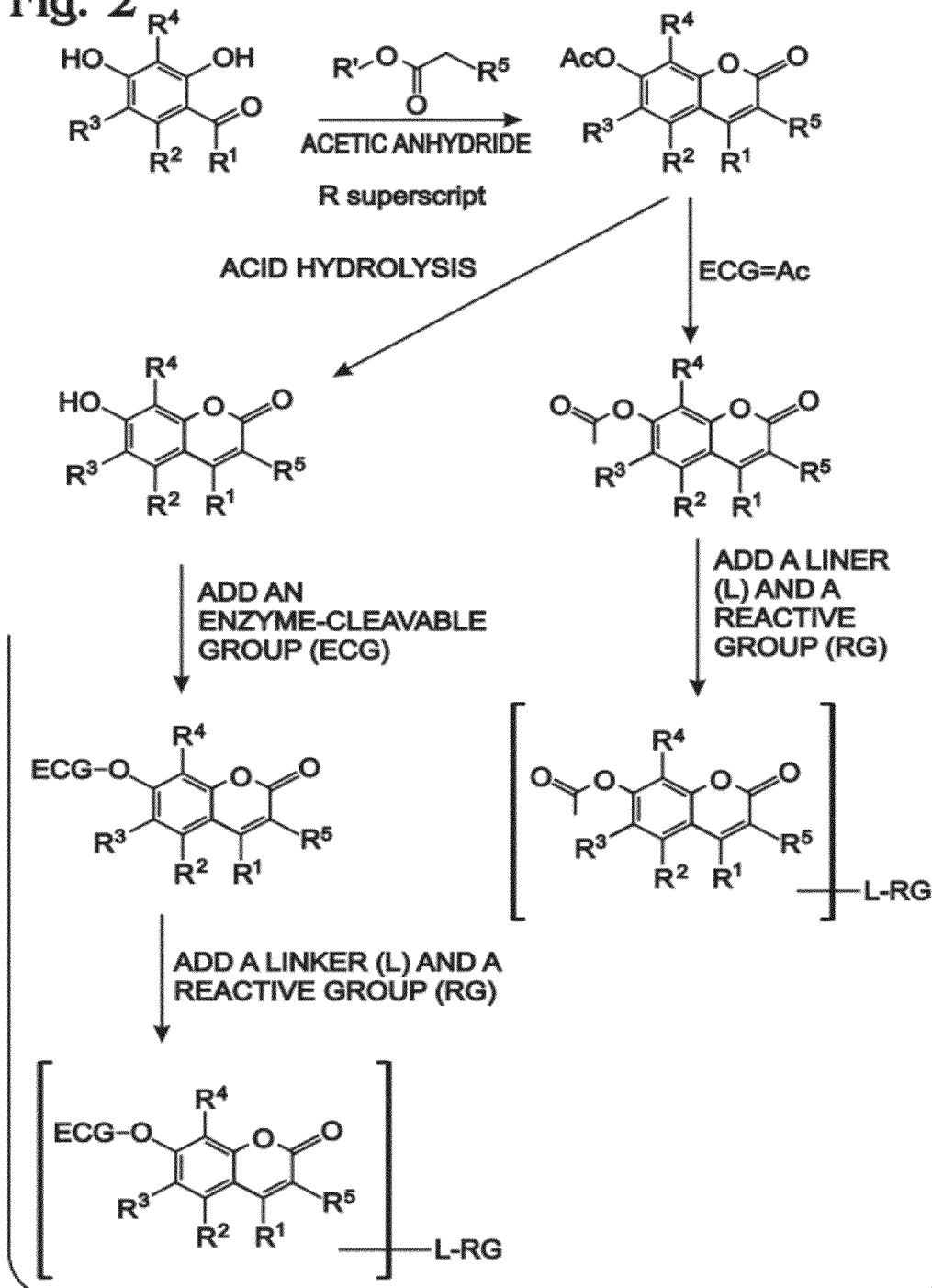
FIG. 2 is a reaction scheme for the synthesis of reactive 7-hydroxycoumarin enzyme substrates by acetic anhydride-based condensation of 4-carbonylresorcinols with heterocycle acetate compound or a carbonylacetate derivative. These basic structures are optionally further substituted, during or after synthesis, to give the desired coumarin enzyme substrate with proper substituents.
Figure 3:
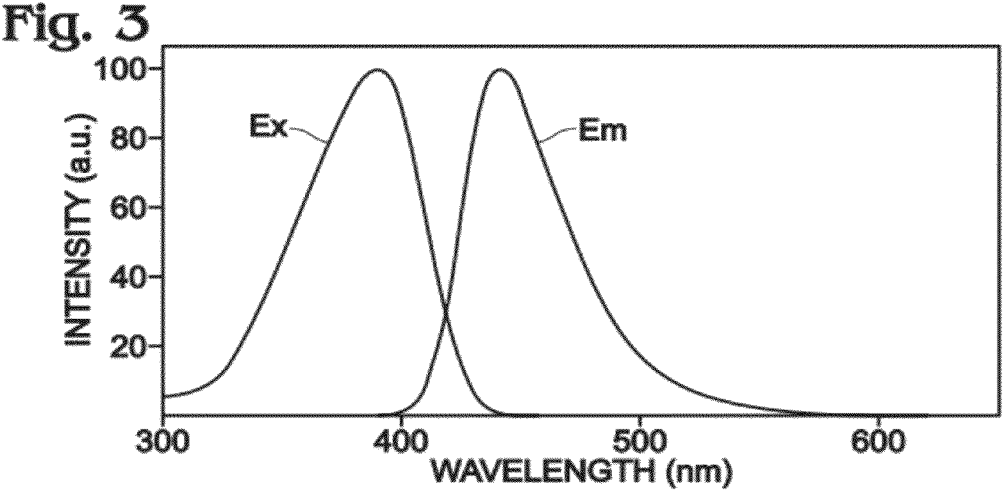
FIG. 3 shows the absorption spectra and emission spectra of ES1 at pH=9.0 buffer after it is incubated with cells. CPA cells are incubated with Compound ES1 (5 µM) for 1 h, and lysed with 1% Triton® X-100. The cell lysates from the enzymatic hydrolysis of Compound ES1 have a maximum absorption around 409 nm, which matches very well the 405 nm violet laser excitation of a typical flow cytometer.
Figure 4:
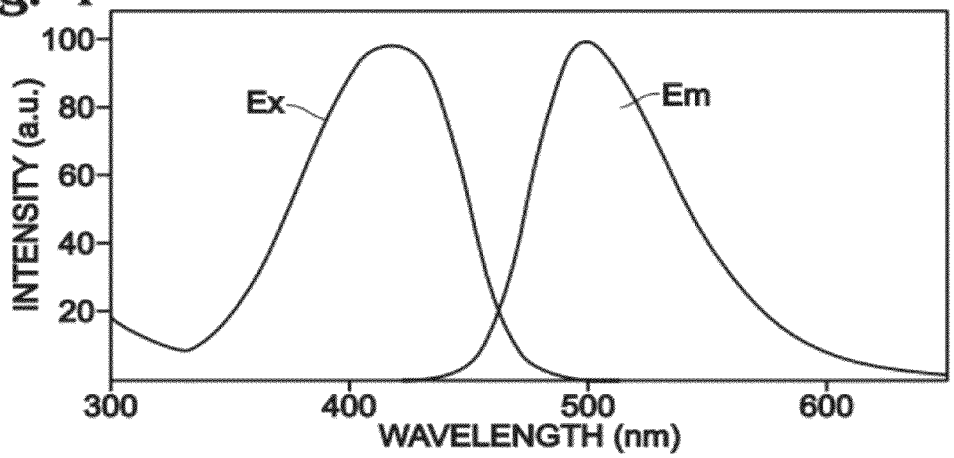
FIG. 4 shows the absorption spectra and emission spectra of ES7 at pH=9.0 buffer after it is incubated with cells. CPA cells are incubated with Compound ES7 (5 µM) for 1 h, and lysed with 1% Triton® X-100. The cell lysates from the enzymatic hydrolysis of ES7 have a maximum absorption around 416 nm, which matches very well the 405 nm violet laser excitation of a typical flow cytometer.

The disclosed 7-Hydroxycoumarin derivatives may be prepared from the acetic anhydride-based condensation of 4-carbonylresorcinols with a heterocycle acetatic acid or carbonylacetate. Alternatively, the base-catalyzed condensation of 4-carbonylresorcinols with active methylene compounds may also be used for the synthesis of 7-hydroxycoumarin derivatives. These basic structures are optionally further substituted, during or after synthesis, to give the corresponding coumarin enzyme substrate with the desired substituents as described above. It is recognized that there are many possible variations that may yield an equivalent results. The typical syntheses of exemplary reactive coumarin enzyme substrates are illustrated in FIGS. 1 and 2. Other known synthetic methods of comarins in the literature might be adapted to prepare chemically reactive coumarins by certain modifications known to the ones skilled in the arts (Bentsen et al., U.S. Pat. No. 6,566,508; Dittmer et al., J. Org. Chem. 2005, 70, 4682; Shi et al., Fen Xi Hua Xue 2005, 33, 1452; Sivakumar et al., Org. Lett 2004, 6, 4603; Zhao et al., J. Am. Chem. Soc. 2004, 126, 4653; Huang et al., J. Chem. Soc. Perkin Trans. 1, 1994, 102; Kuznetsova and Kaliya, Russ. Chem. Rev. 1992, 61, 1243).

The methods for synthesis of coumarin enzyme substrates that contain a variety of reactive groups such as those described in Table 1 are well documented in the art. Particularly useful are amine-reactive enzyme substrates such as "activated esters" of carboxylic acids, which are typically synthesized by coupling a carboxylic acid to a relatively acidic "leaving group." Other preferred amine-reactive groups include sulfonyl halides, which are prepared from sulfonic acids using a halogenating agent such as $PCl_5$ or $POCl_3$; halotriazines, which are prepared by the reaction of cyanuric halides with amines; and isocyanates or isothiocyanates, which are prepared from amines and phosgene or thiophosgene, respectively. Selected embodiments of the disclosure are given in Table 2.

TABLE 2

Selected exemplary compounds of the present disclosure:

| Enzyme Substrate | Structure |
|---|---|
| ES1 | 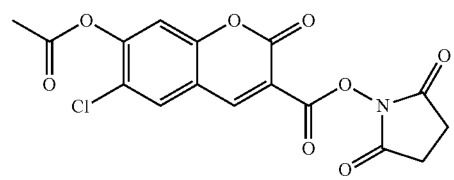 |
| ES2 | 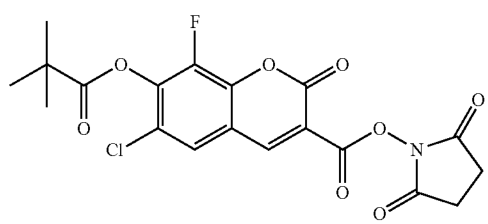 |
| ES3 | 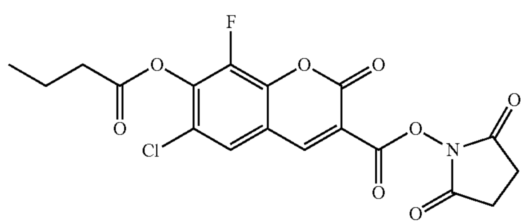 |
| ES4 | 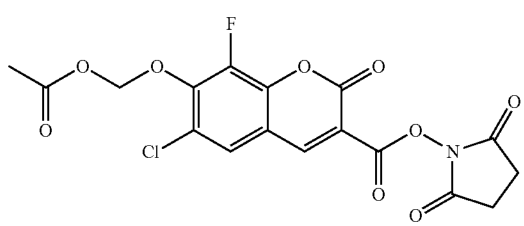 |

TABLE 2-continued

Selected exemplary compounds of the present disclosure:

| Enzyme Substrate | Structure |
|---|---|
| ES5 | 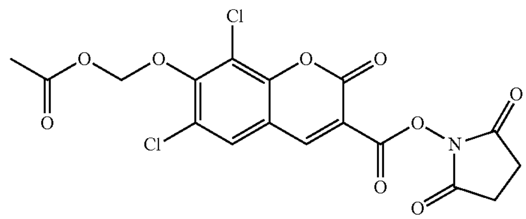 |
| ES6 | 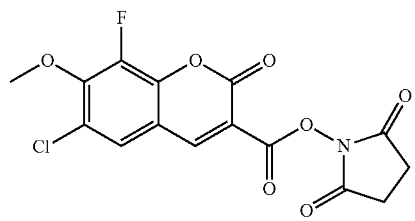 |
| ES7 | 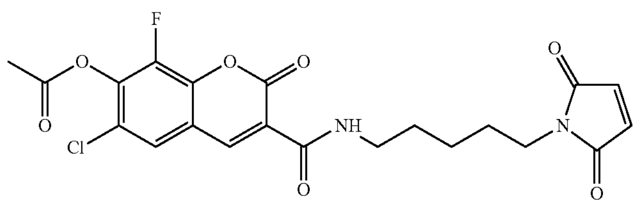 |
| ES8 | 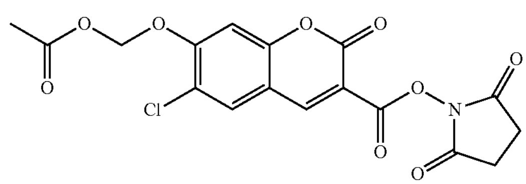 |
| ES9 | 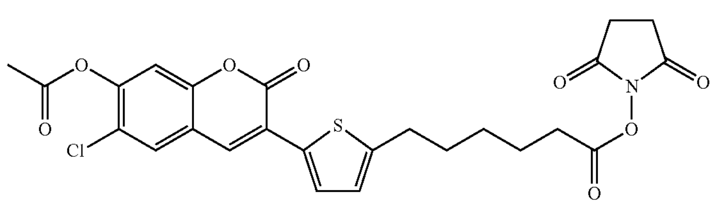 |
| ES10 | 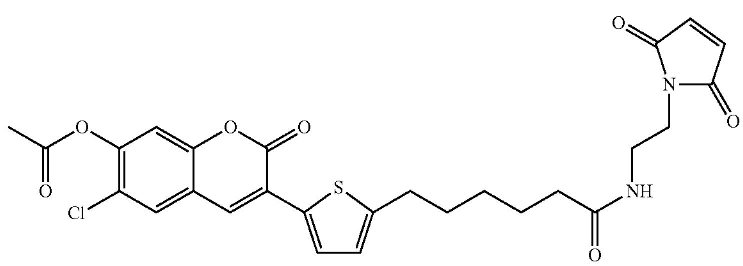 |
| ES11 | 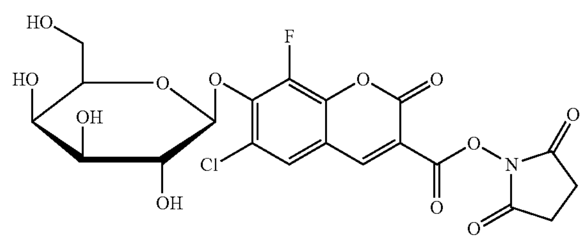 |

TABLE 2-continued
Selected exemplary compounds of the present disclosure:
| Enzyme Substrate | Structure |
|---|---|
| ES12 | 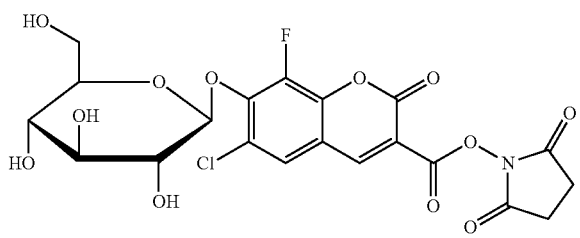 |
| ES13 | 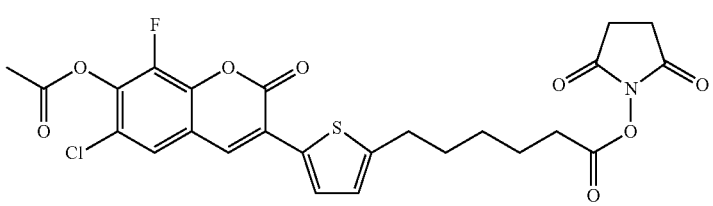 |
| ES14 | 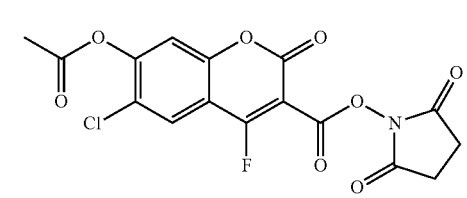 |
| ES15 | 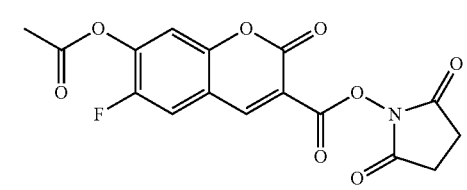 |
| ES16 | 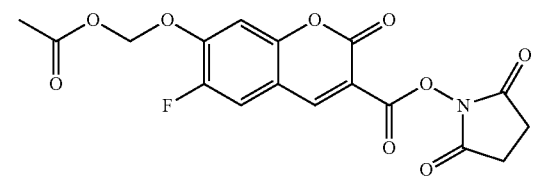 |
| ES17 | 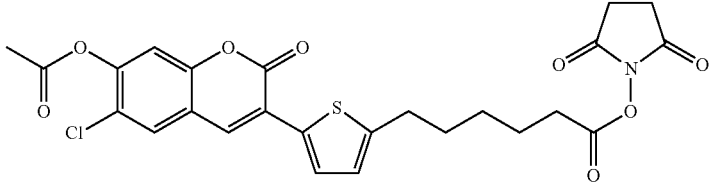 |
| ES18 | 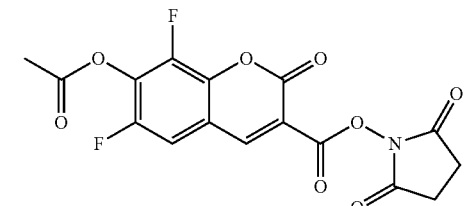 |

TABLE 2-continued

Selected exemplary compounds of the present disclosure:

| Enzyme Substrate | Structure |
|---|---|
| ES19 | 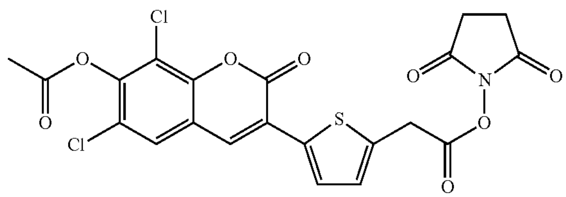 |
| ES20 | 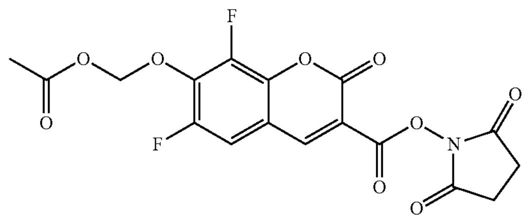 |
| ES21 | 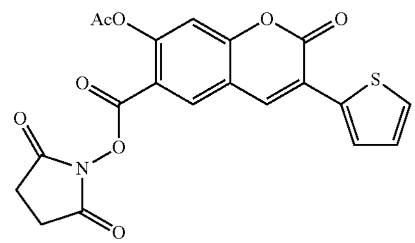 |
| ES22 | 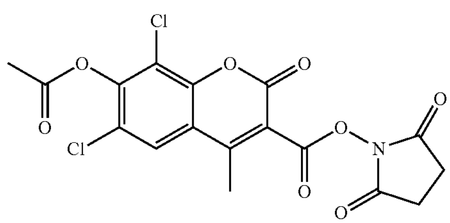 |
| ES23 | 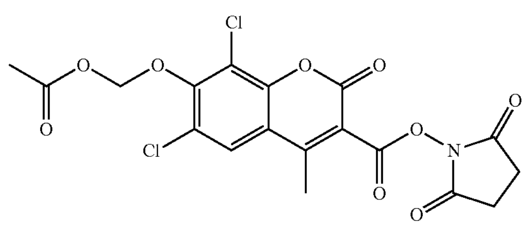 |
| ES24 | 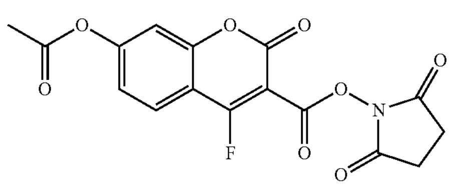 |
| ES25 | 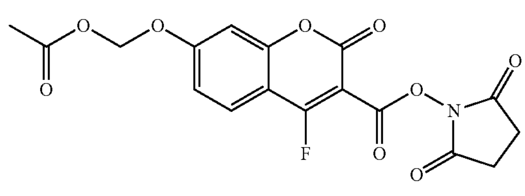 |

TABLE 2-continued
Selected exemplary compounds of the present disclosure:
| Enzyme Substrate | Structure |
|---|---|
| ES26 | 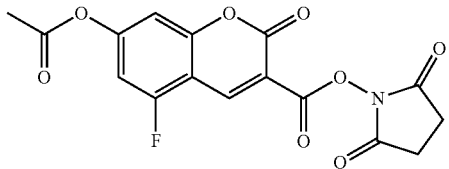 |
| ES27 | 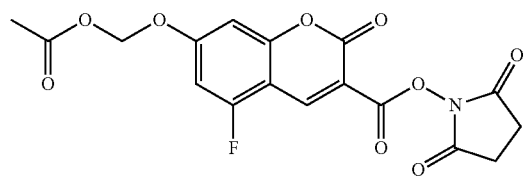 |
| ES28 | 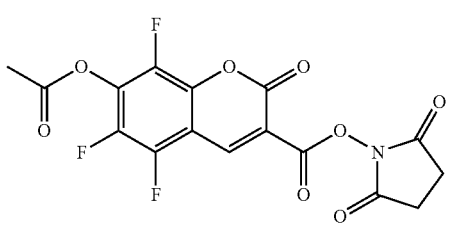 |
| ES29 | 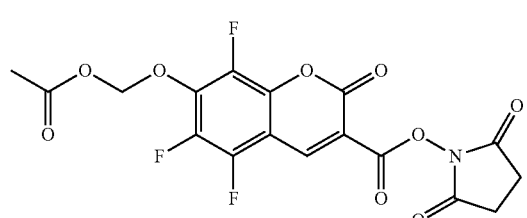 |
| ES30 | 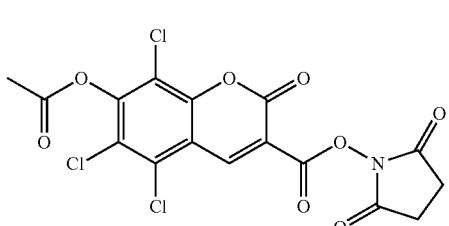 |
| ES31 | 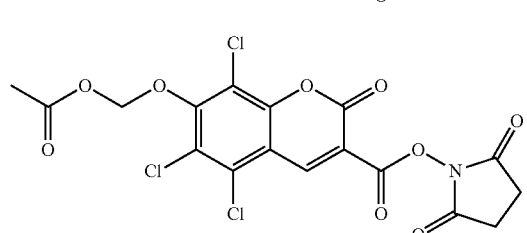 |
| ES32 | 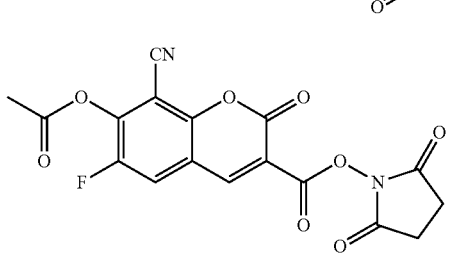 |

TABLE 2-continued

Selected exemplary compounds of the present disclosure:

| Enzyme Substrate | Structure |
|---|---|
| ES33 | 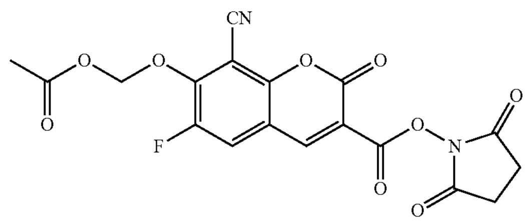 |
| ES34 | 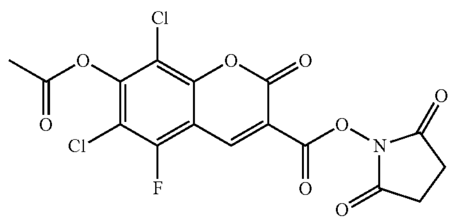 |
| ES35 | 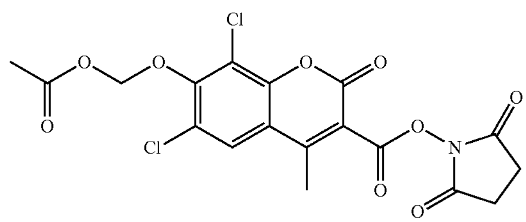 |
| ES36 | 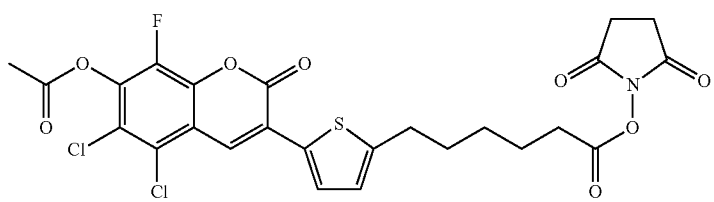 |
| ES37 | 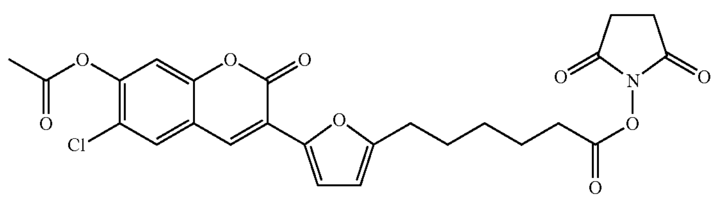 |
| ES38 | 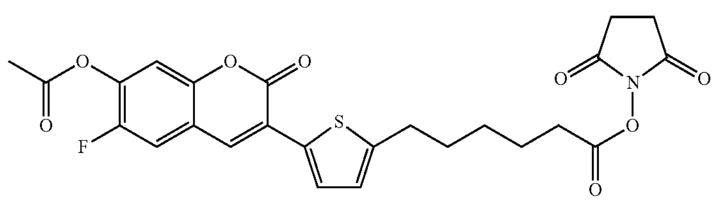 |
| ES39 | 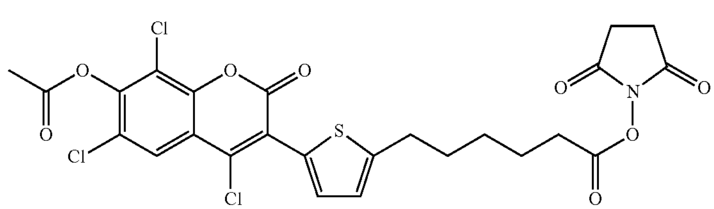 |

TABLE 2-continued

Selected exemplary compounds of the present disclosure:

| Enzyme Substrate | Structure |
| --- | --- |
| ES40 | 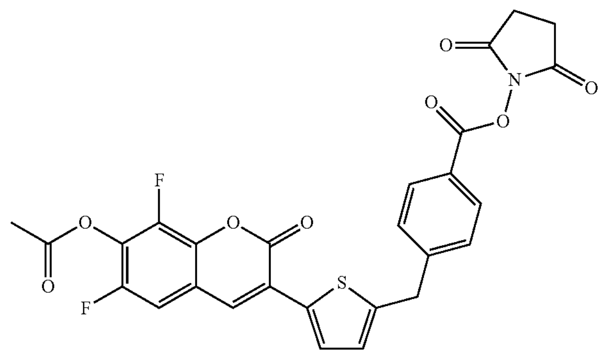 |
| ES41 | 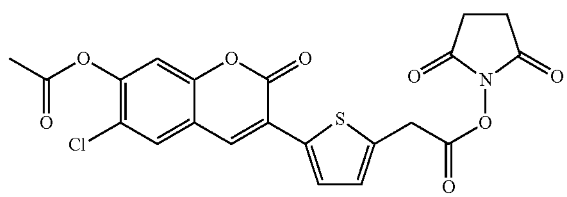 |
| ES42 | 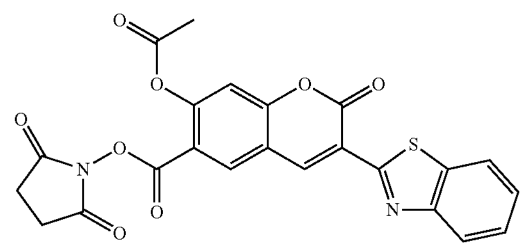 |
| ES43 | 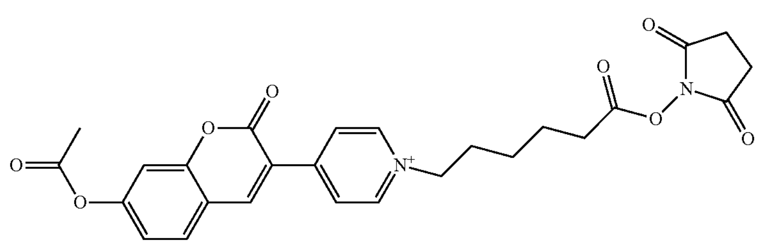 |
| ES44 | 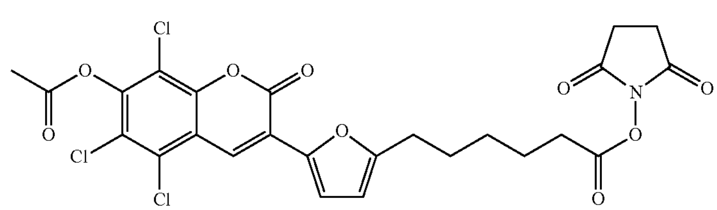 |
| ES45 | 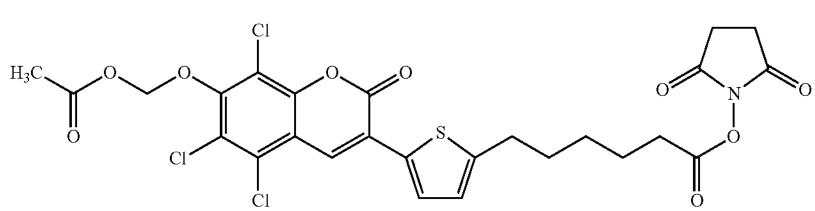 |

TABLE 2-continued

Selected exemplary compounds of the present disclosure:

| Enzyme Substrate | Structure |
|---|---|
| ES46 | (structure) |
| ES47 | (structure) |
| ES48 | (structure) |
| ES49 | (structure) |
| ES45 | (structure) |
| ES46 | (structure) |

TABLE 2-continued

Selected exemplary compounds of the present disclosure:

| Enzyme Substrate | Structure |
|---|---|
| ES47 | 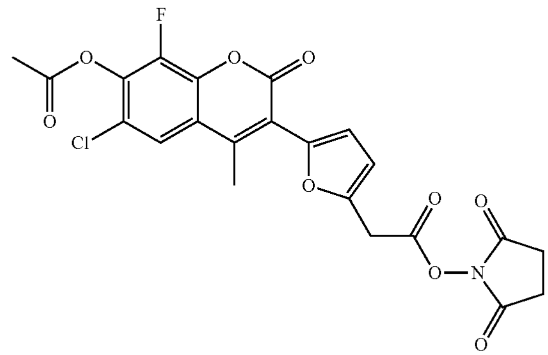 |
| ES48 | 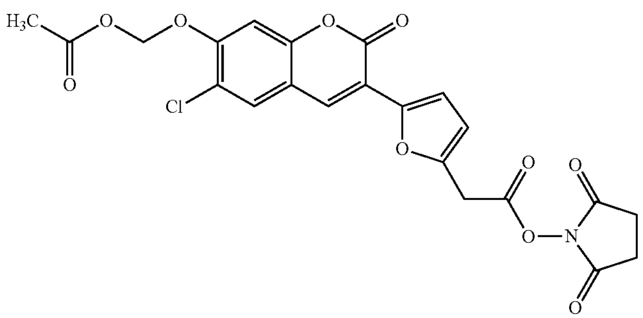 |
| ES49 | 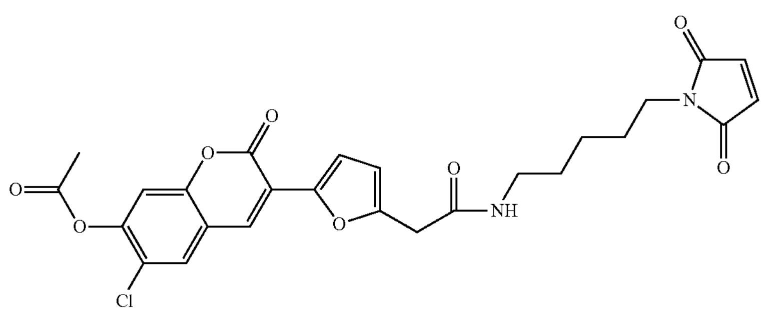 |
| ES50 | 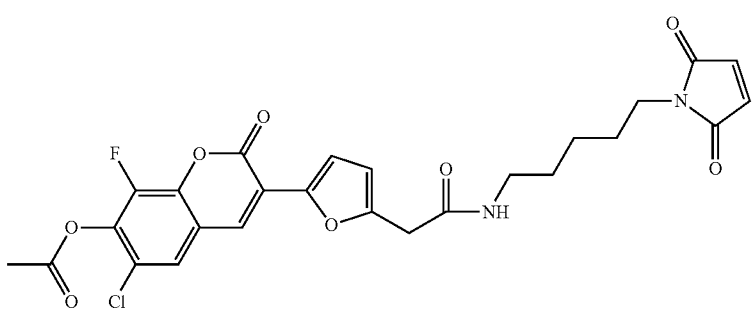 |
| ES51 | 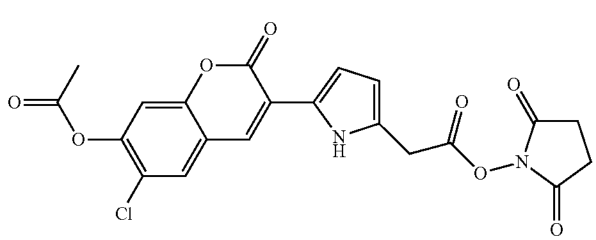 |

TABLE 2-continued

Selected exemplary compounds of the present disclosure:

| Enzyme Substrate | Structure |
|---|---|
| ES52 | 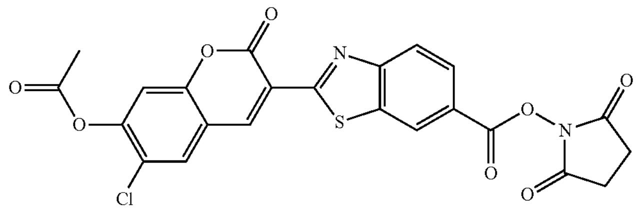 |
| ES53 | 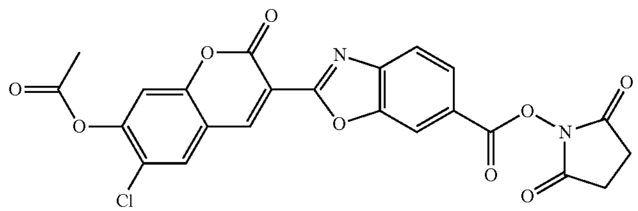 |
| ES54 | 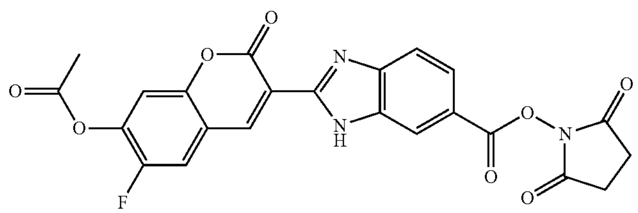 |
| ES55 | 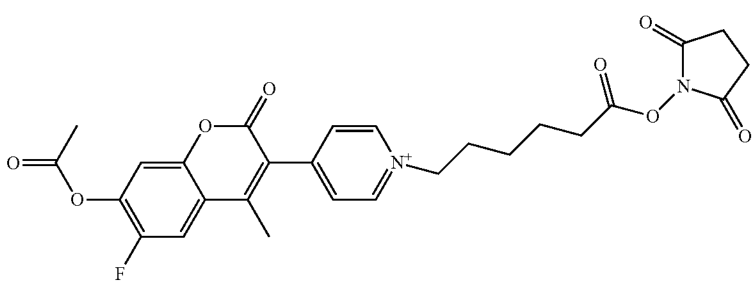 |
| ES56 | 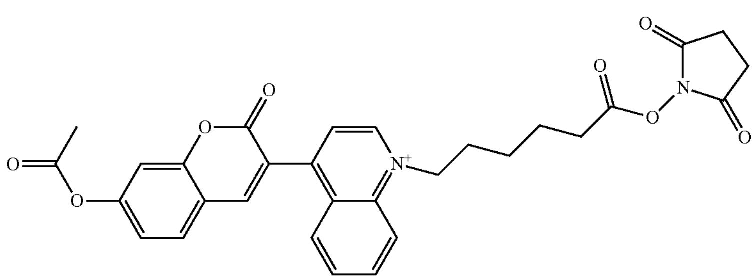 |
| ES57 | 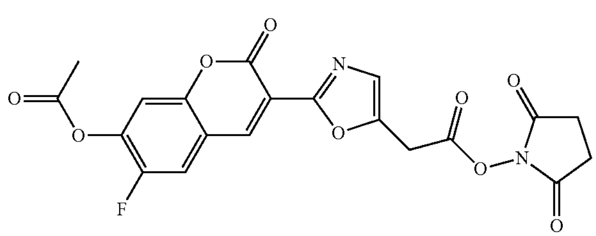 |

TABLE 2-continued

Selected exemplary compounds of the present disclosure:

| Enzyme Substrate | Structure |
|---|---|
| ES58 | 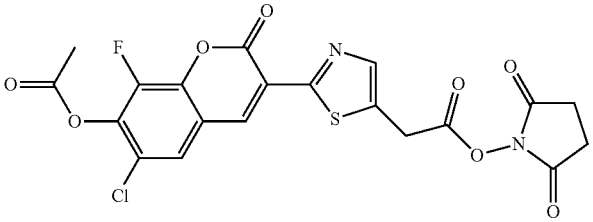 |

Applications and Methods of Use

The enzyme substrate compounds disclosed herein are particularly suitable for directly staining or labeling live cells, so that the cells can subsequently be identified or quantitated. In one aspect, the enzyme substrates may be used to stain cells that include a component with which the selected fluorogenic substrate and/or its fluorescent enzymatic product react, thereby keeping the fluorophore from leaking out of cells.

The enzyme substrate compounds disclosed herein are generally utilized by combining an enzyme substrate compound as described above with sample of interest that contains or is thought to contain cells, under conditions selected to yield a detectable optical response. The term "enzyme substrate compound" is used herein to refer to all aspects of the disclosed enzyme substrates. The enzyme substrate compound may form a covalent or non-covalent association or complex with an element of the cells within the sample of interest, or may form an association or complex with an element that is simply present within the bounds of the cells. The cells are then illuminated at a wavelength selected to elicit a detectable optical response. Typically, staining the cells with an enzyme substrate compound of the disclosure is used to determine a specified characteristic of the cells by further comparing the detectable optical response with a standard or expected response.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining compared with a standard or expected response, indicates whether and to what degree the sample possesses a given characteristic. Some enzyme substrates of the disclosure may exhibit little fluorescence emission, but are still useful as chromophoric enzyme substrates. Such chromophores are useful as energy acceptors in FRET applications, or to simply impart the desired color to a sample or portion of a sample.

For biological applications, the enzyme substrate compounds of the disclosure are typically used in an aqueous, mostly aqueous or aqueous-miscible solution prepared according to methods generally known in the art. The exact concentration of enzyme substrate compound needed for a given application is usually dependent upon the experimental conditions and the desired results, but typically ranges from about one nanomolar to one millimolar or more. The optimal concentration is determined by systematic variation until satisfactory results with minimal background fluorescence are accomplished.

The enzyme substrate compounds are most advantageously used to stain cells. The cells may comprise heterogeneous mixtures of components (including intact cells, cell extracts, bacteria, viruses, organelles, and mixtures thereof), or a single component or homogeneous group of components (e.g., natural or synthetic amino acid, nucleic acid or carbohydrate polymers, or lipid membrane complexes). These enzyme substrates are generally non-toxic to living cells and other biological components, within the concentrations of use.

The enzyme substrate compound is combined with the sample in any way that facilitates contact between the enzyme substrate compound and the sample components of interest. Typically, the enzyme substrate compound or a solution containing the enzyme substrate compound is simply added to the sample. Enzyme substrate compounds that possess a lipophilic substituent, such as phospholipids, will non-covalently incorporate into lipid assemblies, e.g. for use as probes for membrane structure; or for incorporation in liposomes, lipoproteins, films, plastics, lipophilic microspheres or similar materials; or for tracing. Lipophilic enzyme substrates are useful as fluorescent probes of membrane structure.

Chemically reactive enzyme substrate compounds will covalently attach to a corresponding functional group of cell components, forming the complexes of enzyme substrates-cell components or enzyme products-cell components. Using enzyme substrate compounds to label reactive sites on the surface of cells, in cell membranes or in intracellular compartments such as organelles, or in the cell's cytoplasm, permits the determination of their presence or quantity, accessibility, or their spatial and temporal distribution in the sample. Substrates E1, 4, 5, 8, 9 and 10 are more stable than Compound ES 18, which is cleaved by intracellular esterases more slowly. Photoreactive enzyme substrates can be used similarly to photolabel components of the outer membrane of biological cells or as photo-fixable polar tracers for cells.

Optionally, the sample is washed after staining to remove residues, excess or unbound enzyme substrate compound. The sample is optionally combined with one or more other solutions in the course of staining, including wash solutions, permeabilization and/or fixation solutions, and solutions containing additional detection reagents. An additional detection reagent typically produces a detectable response due to the presence of a specific cell component, intracellular substance, or cellular condition, according to methods generally known in the art. Where the additional detection reagent has, or yields a product with, spectral properties that differ from those of the subject enzyme substrate compounds, multicolor applications are possible. This is particularly useful where the additional detection reagent is an enzyme substrate or enzyme substrate-conjugate of the present disclosure having spectral properties that are detectably distinct from those of the staining enzyme substrate.

At any time after or during staining, the sample may be illuminated with a wavelength of light selected to give a detectable optical response, and observed with a means for detecting the optical response. Equipment that may be useful for illuminating the enzyme substrate compounds of the disclosure includes, but is not limited to, hand-held ultraviolet lamps, mercury arc lamps, xenon lamps, lasers and laser diodes. These illumination sources are optionally integrated into laser scanners, fluorescence microplate readers, standard or mini-fluorometers, chromatographic detectors, or other instrumentation. Preferably, the enzyme substrates of the disclosure are excitable at or near 405 nm, as this region closely match the output of the relatively inexpensive violet laser excitation source.

The detectable optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes, among other devices. Where the sample is examined using a flow cytometer, examination of the sample optionally includes sorting portions of the sample according to their fluorescence response.

One aspect of the instant disclosure is the formulation of kits that facilitate the practice of various assays using any of the enzyme substrates of the disclosure, as described above. The kits of the disclosure typically include a chromogenic or fluorogenic enzyme substrate compound of the present disclosure. The kit optionally further includes one or more buffering agents, typically present as an aqueous solution. The kits of the disclosure optionally further include one or more additional detection reagents, one or more antibody reagents as an additional color for multicolor applications, luminescence standards, enzymes, enzyme inhibitors, organic solvents, or instructions for carrying out an assay of the disclosure.

Although the present invention has been shown and described with reference to the foregoing structures, syntheses, applications, and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

EXAMPLES

Selected examples of synthetic strategies for selected enzyme substrates of the disclosure, as well as their characterization, synthetic precursors, substrates and method of use are provided in the examples below. Further modifications and permutations will be obvious to one skilled in the art. The examples below are given so as to illustrate the practice of this disclosure. They are not intended to limit or define the entire scope of this disclosure.

Example 1

Preparation of Compound 1

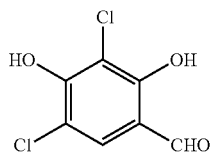

Compound 1

2,4-Dichlororesorcinol (50 g, Shaanxi Zhendi Chemical Biology, Ltd.) is dissolved in dry ether (200 ml). To the solution are added finely powdered zinc cyanide (50 g) and potassium chloride (12 g) with stirring. The suspension is cooled to 0° C. A strong stream of hydrogen chloride gas is blown into the solution with vigorous stirring. After approximately 1-2 hours the reactants are dissolved. The addition of hydrogen chloride gas is continued until it stops being absorbed in the ether solution. The suspension is stirred for one additional hour on ice. The ether solution is poured from the solid that is treated with ice and heated to 100° C. in a water bath. Upon cooling the product crystallized in shiny plates from the solution, which is removed by filtration and air-dried to give the desired Aldehyde 1.

Example 2

Preparation of Compound 2

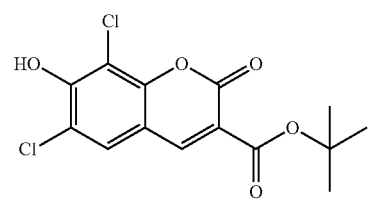

Compound 2

Compound 1 (7 g), tert-butyl methyl malonate (6 g), 0.5 ml of piperidine and 0.3 ml of acetic acid are heated under reflux for three hours in 100 ml of methanol. After cooling to room temperature, the mixture is filtered and the filtrate is concentrated. The concentrated filtrated is poured into water, and resulted precipitate is filtered off with suction to collect the solid that is air-dried. The crude product is further purified with silica gel chromatography to yield the desired Compound 2.

Example 3

Preparation of Compound 3

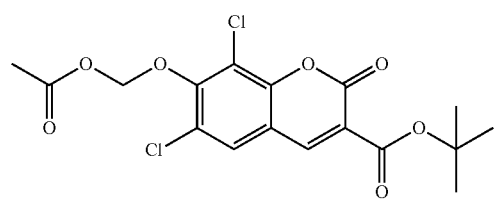

Compound 3

Compound 2 (500 mg) is dissolved in anhydrous DMF (2 mL) at RT. To the DMF solution of Compound 2, BrCH2OAc (750 mg) is slowly added while stirring in a water bath. To the resulted mixture iPr$_2$NEt (150 µL) is added slowly. The resulted mixture is stirred for 24-36 h. The reaction mixture is poured into ice/water. The suspension is filtered to collect the solid that is washed with water. The dried solid is purified on a silica gel column to give Compound 3 using a gradient of chloroform/ethyl acetate.

Example 3

Preparation of Compound 4

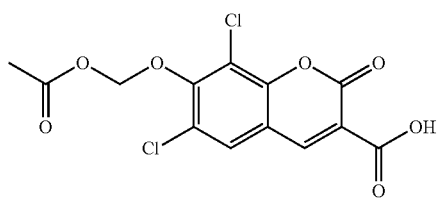

Compound 4

Compound 3 (300 mg) is dissolved in anhydrous dioxane (25 mL) at RT. To the dioxane solution of Compound 3, anisole (50 mg) is added in one portion, followed by the slow addition of 4M HCl in dioxane (5 ml). The resulted mixture is stirred until most of Compound 3 is consumed. The reaction mixture is poured into ice/water, and neutralized to pH 4-5 by sodium bicarbonate. The suspension is filtered to collect the solid that is washed with water. The dried solid is purified on a silica gel column to give Compound 4 using a gradient of chloroform/methanol.

Example 5

Preparation of Compound 5

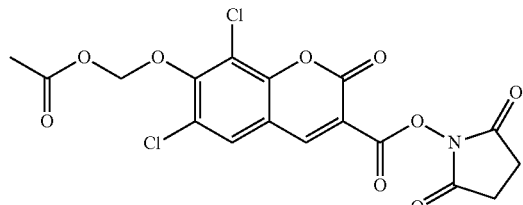

Compound 5

Compound 4 (70 mg) and N,N'-disuccinimidyl carbonate (80 mg) are dissolved in DMF (5 ml). To the DMF solution is added triethylamine (1.2 ml) and 4-dimethylaminopyridine (2 mg). The resulted solution is stirred at room temperature until Compound 4 is completely consumed. The mixture is filtered and the filtrate is concentrated. The concentrated filtrated is poured into water, and resulted precipitate is filtered off with suction to collect the solid that is washed with water and air-dried to yield the desired Compound 5.

Example 6

Preparation of Compound 6

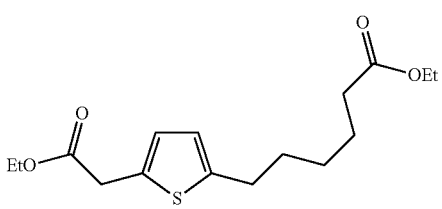

Compound 6

Ethyl 2-thiopheneneacetate (10 g) and ethyl 6-bromohexanoate (12 g) are dissolved in dichloromethane (200 ml). To the solution is added anhydrous $AlCl_3$ (24 g) under dry nitrogen protection with vigorous stirring at 0° C. The reaction mixture is stirred under dry nitrogen protection at 0° C., and warmed to room temperature when the reaction is complete as indicated by TLC. The reaction mixture is poured into ice-water, and extracted with chloroform (3×200 ml). The chloroform layers are combined, dried over anhydrous $Na_2SO_4$, and the solvent is removed under vacuum to give a crude solid. The crude solid is further purified on a silica gel column with a gradient of chloroform/ethyl acetate as eluant to yield the desired Compound 6.

Example 7

Preparation of Compound 7

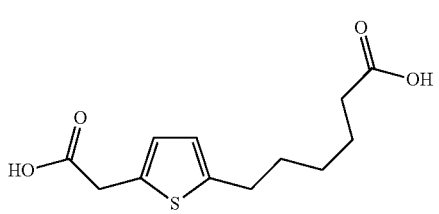

Compound 7

Compound 6 (10 g) is dissolved in ethanol (100 ml). To the solution is added 5 M NaOH (65 ml). The reaction mixture is stirred at room temperature, and neutralized with concentrated HCl when the reaction is complete as indicated by TLC. The resulted mixture is extracted with ethyl acetate (3×200 ml). The ethyl acetate layers are combined, dried over anhydrous $Na_2SO_4$, and the solvent is removed under vacuum to give the desired Compound 7.

Example 8

Preparation of Compound 8

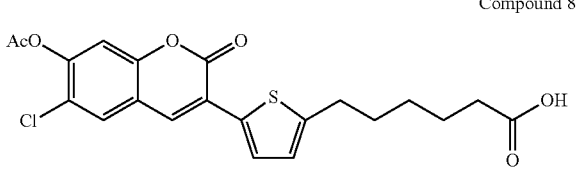

Compound 8

Compound 1 (6 g) and Compound 7 (5.8 g) are suspended in acetic anhydride (100 ml). To the suspension triethylamine (6 ml) is added at room temperature. The reaction mixture is heated at 120-140° C. until the reaction is complete as indicated by TLC. After cooling to room temperature, the mixture is poured into ice-water, and resulted precipitate is filtered off

Example 9

Preparation of Compound 9

Compound 9

Compound 8 (100 mg) and succinimidyl trifluoroacetate (110 mg) are dissolved in DMF (5 ml). To the solution is added is added anhydrous triethylamine (0.1 ml) under dry nitrogen protection with vigorous stirring at room temperature. The reaction mixture is stirred under dry nitrogen protection at room temperature until the reaction is complete as indicated by TLC. The reaction mixture is poured into water, and the resulted precipitate is collected by filtration. The solid is washed with water, and dried to yield the desired Compound 9.

Example 10

Preparation of Compound 10

Compound 10

To Compound 9 (10 mg) in DMF (0.2 ml) at room temperature is added 4 equivalents of triethylamine and 1.2 equivalents of N-(2-aminoethyl)maleimide, trifluoroacetic acid salt (Aldrich). The mixture is stirred at ambient temperature for 60 minutes. The DMF solution is poured into water, and resulted suspension is centrifuged to collect the solid that is air-dried. The crude product is further purified with silica gel chromatography to yield the desired Compound 10.

Example 11

Preparation of Compound 11

Compound 11

Compound 11 is prepared from 4-chloro-2-fluororesorcinol (Yang et al., Current Chem. Genomics, 2008, 48) analogous to the procedure of Compound 1.

Example 12

Preparation of Compound 12

Compound 12

Compound 12 is prepared from the condensation of Compound 11 with Compound 7 analogous to the procedure of Compound 8.

Example 13

Preparation of Compound 13

Compound 13

Compound 13 is prepared from the condensation of Compound 12 with N,N'-disuccinimidyl carbonate analogous to the procedure of Compound 9.

Example 14

Preparation of Compound 14

Compound 14

Ethyl 2-thiopheneneacetate (5 g) and methyl 4-bromomethylbenzoate (6.2 g) are dissolved in dichloromethane (200 ml). To the solution is added is added anhydrous AlCl$_3$ (12 g) under dry nitrogen protection with vigorous stirring at 0° C. The reaction mixture is stirred under dry nitrogen protection at 0° C., and warmed to room temperature when the reaction is complete as indicated by TLC. The reaction mixture is poured into ice-water, and extracted with chloroform (3×200 ml). The chloroform layers are combined, dried over anhydrous $Na_2SO_4$, and the solvent is removed under vacuum to give a crude solid. The crude solid is further purified on a silica gel column with a gradient of hexanes/ethyl acetate as eluant to yield the desired Compound 14.

Example 15

Preparation of Compound 15

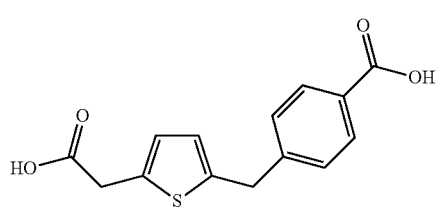

Compound 15

Compound 14 (5 g) is dissolved in ethanol (50 ml). To the solution is added 5 M NaOH (65 ml). The reaction mixture is stirred at room temperature, and neutralized with concentrated HCl when the reaction is complete as indicated by TLC. The reaction mixture is extracted with ethyl acetate (3×200 ml). The ethyl acetate layers are combined, dried over anhydrous $Na_2SO_4$, and the solvent is removed under vacuum to give the desired Compound 15.

Example 16

Preparation of Compound 16

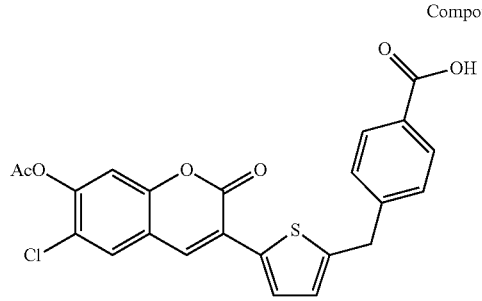

Compound 16

Compound 16 is prepared from the condensation of 4-chlororesorcinol with Compound 15 analogous to the procedure of Compound 8.

Example 17

Preparation of Compound 17

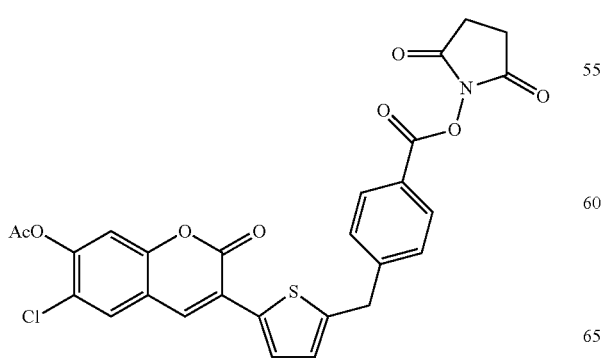

Compound 17

Compound 17 is prepared from the condensation of Compound 16 with N,N'-disuccinimidyl carbonate analogous to the procedure of Compound 9.

Example 18

Preparation of Compound 18

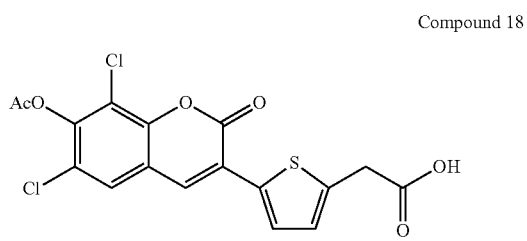

Compound 18

Compound 1 (1 g) and 2,5-dicarboxymethylthiophene (6 g, Aldrich) are suspended in acetic anhydride (100 ml). To the suspension triethylamine (6 ml) is added at room temperature. The resulted reaction mixture is heated at 120-140° C. until the reaction is complete as indicated by TLC. After cooling to room temperature, the mixture is poured into ice-water, and resulted precipitate is filtered off with suction to collect the solid that is air-dried. The crude solid is further purified on a silica gel column with a gradient of chloroform/methanol as eluant to yield the desired Compound 18.

Example 19

Preparation of Compound 19

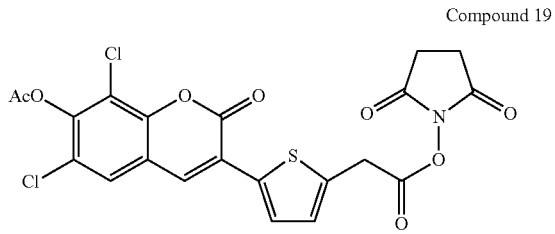

Compound 19

Compound 19 is prepared from the condensation of Compound 18 with N,N'-disuccinimidyl carbonate analogous to the procedure of Compound 9.

Example 20

Preparation of Compound 20

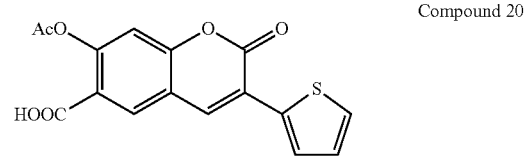

Compound 20

Compound 20 is prepared from the condensation of 2,4-dihydroxy-5-formylbenzoic acid (Fanbo Biochemicals, Ltd.) with 2-thiopheneacetic acid analogous to the procedure of Compound 8.

Example 21

Preparation of Compound 21

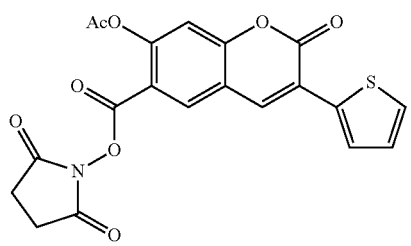

Compound 21

Compound 21 is prepared from the condensation of Compound 20 with N,N'-disuccinimidyl carbonate analogous to the procedure of Compound 9.

Example 22

Analyzing Cell Proliferations with Substrate ES1, 4, 5, 8, 9 or 10

Figure 6:
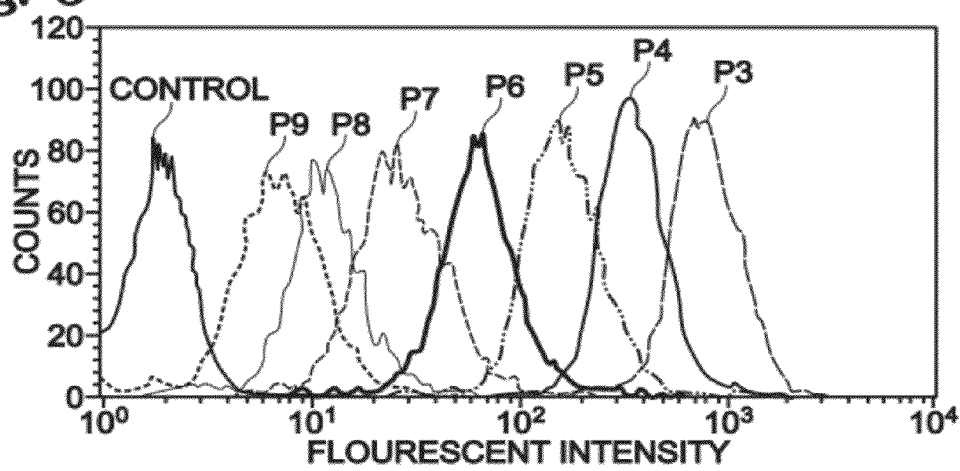
FIG. 6 shows the staining of cells using compound ES 9. Compound ES 9 is dissolved in anhydrous DMSO to make 5 mM stock solution, and diluted in PBS buffer to make 5 µM dye loading solution. Jurkat cells are loaded with the dye loading solution of Compound ES9 at 37° C. for 1 hour. The cells are washed with PBS buffer to remove serum. The resulted cells are cultured and passed for flow cytometric analysis as desired. Compound ES9 is used to monitor cell proliferation of nine passages.

ES compounds are retained by cells and shared by the daughter cells at each division, resulting in multimodal flow cytometric ES staining histograms, with each cell generation clustering around half the fluorescence intensity of the previous one. ES compounds are dissolved in anhydrous DMSO, and the stock solutions are used promptly. To prepare the cell working solutions (from 1 to 100 μM) the DMSO stock solutions of ES compounds are diluted with Hanks and 20 mM Hepes buffer (HHBS, pH 7 with 0.02% PF-127). The Jurkat cells are treated with test compounds for a desired period of time, and centrifuged give $1-5 \times 10^5$ cells per tube. The cells are resuspended in 500 μL of the ES compound working solutions, and incubated at room temperature or 37° C. for 5 to 10 min. The ES compound working solutions are removed from the cells that are washed with HHBS. The cells are resuspended in 500 μL of prewarmed HHBS or medium to give $1-5 \times 10^5$ cells per tube. The fluorescence of ES compound staining are monitored at Ex/Em=405/450 nm, 405/500 nm or 405/550 nm with a fluorescence microscope or a flow cytometer. Fluorescence imaging analysis of cell proliferations with Compound ES1 is shown in FIG. 5. Flow cytometric analysis of cell proliferations with Compound ES1 is shown in FIG. 6.

Example 23

Tracking the Distribution of Peritoneal B-Cell Subsets with Substrate ES1, 4, 5, 8, 9 or 10 in Vivo Peritoneal B cells represent a heterogeneous mixture of mature peripheral B lineage subsets with distinct developmental and functional characteristics. Substrate ES1, 4, 5, 8, 9 or 10 is used for labeling lymphocytes. Using this in situ labeling procedure followed by multicolor flow cytometry or tissue fluorescence at various periods the distinct peritoneal leukocyte sub-populations have different exchange kinetics. The B cells labeled with the ES compounds demonstrate only minimal localization to other peripheral lymphoid tissues.

Example 24

In Vitro Tracing of Rat Bone Marrow Mesenchymal Stem Cells with Substrate ES1, 4, 5, 8, 9 or 10

Rat MSCs were labeled with ES compounds at different concentrations (from 1 to and 100 μM) for 1 to 30 min. The fluorescence intensity in the cells were measured by flow cytometry and fluorescence microscope to determine the optimal condition for MSC labeling. Under the optimal condition, the effect of ES compounds on the growth of MSCs is evaluated by flow cytometry and fluorescence microscope to determine the maximum time length following ES compound. The cell labeling of ES compounds allow MSC tracing. Staining with ES compounds from 10 to 30.0 micromol/L for 5 to 10 min is effective for labeling rat MSCs in vitro.

Example 25

Tracking Cell Proliferations with Substrate ES1, 4, 5, 8, 9 or 10

ES compounds are retained by cells and shared by the daughter cells at each division, resulting in multimodal flow cytometric ES staining histograms, with each cell generation clustering around half the fluorescence intensity of the previous one. IGROV1 ovarian cancer cells are loaded with ES compounds at the time of seeding. After a period time cells are treated with a anticancer drug. Effects of anti-cancer drug on IGROV1 cells are analyzed in terms of the time course of the percentage of cells that remained undivided or enter the second, third, and subsequent division cycles. A simple algorithm, which combines flow cytometric data with the absolute cell number independently measured by Coulter counter, provides an estimate of the outcome of the starting cell population by quantifying undivided, divided and dead cells.

Although the present invention has been shown and described with reference to specific compounds, formulations, and applications, it will be apparent to those skilled in the art that various changes in structure, substitution, details of procedure and other aspects of the present disclosure without departing from the spirit and scope of the invention. The present invention is intended to embrace all such alternatives, modifications and variances that fall within the scope of the appended claims.

What is claimed is:
1. A coumarin compound of the formula:

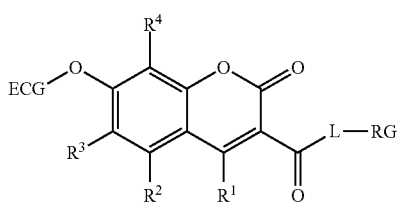

wherein ECG is an acetyl, acetoxymethyl, acetoxyalkylmethyl, acetoxyarylmethyl or a low acyl of 3-10 carbon atoms; L is a linker; RG is a chemically reactive group; $R^1$, $R^2$, $R^3$ and $R^4$ are independently H, halogen, alkyl, alkoxy, aryloxy, thiol, alkylthiol, arylthiol, azido, amino, hydroxyl or boronic acid, RG or L-RG provided that $R^3$ and $R^4$ are not simultaneously H or F; and, wherein the —(C=O)-L-RG moiety is a succinimidyl ester, nitrophenol ester, polychlorophenol ester, or polyfluorophenol ester.

2. The coumarin compound of claim 1 wherein the —(C=O)-L-RG moiety is a succinimidyl ester.

3. The coumarin compound of claim 2 wherein ECG is acetyl.

4. The coumarin compound of claim 3 wherein the compound is of the following structure:

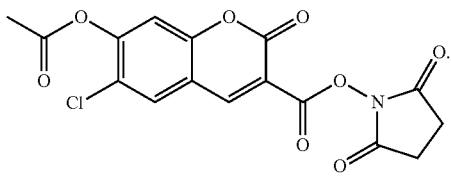

* * * * *